(12) United States Patent
Hamada et al.

(10) Patent No.: US 8,347,743 B2
(45) Date of Patent: Jan. 8, 2013

(54) SPECIMEN PROCESSING DEVICE AND SPECIMEN PROCESSING METHOD

(75) Inventors: Yuichi Hamada, Kobe (JP); Takaaki Nagai, Kobe (JP); Masaharu Shibata, Kobe (JP)

(73) Assignee: Sysmex Corporation, Kobe (JP)

( * ) Notice: Subject to any disclaimer, the term of this patent is extended or adjusted under 35 U.S.C. 154(b) by 214 days.

(21) Appl. No.: 12/775,866

(22) Filed: May 7, 2010

(65) Prior Publication Data

US 2010/0282003 A1 Nov. 11, 2010

(30) Foreign Application Priority Data

May 7, 2009 (JP) ................................. 2009-112825
Jul. 30, 2009 (JP) ................................. 2009-177821

(51) Int. Cl.
*B01L 3/02* (2006.01)
(52) U.S. Cl. .................................................. 73/864.21
(58) Field of Classification Search .................. None
See application file for complete search history.

(56) References Cited

U.S. PATENT DOCUMENTS

| 5,209,903 | A | | 5/1993 | Kanamori et al. | |
| 5,985,215 | A | * | 11/1999 | Sakazume et al. | 422/67 |
| 2003/0215362 | A1 | * | 11/2003 | Sato et al. | 422/63 |
| 2009/0223308 | A1 | | 9/2009 | Fukuma | 73/863.01 |
| 2009/0223311 | A1 | | 9/2009 | Hamada et al. | 73/863.92 |

FOREIGN PATENT DOCUMENTS

| JP | 401223354 | * | 9/1989 |
| JP | 11-316238 A | | 11/1999 |
| JP | 2000-088860 A | | 3/2000 |

* cited by examiner

*Primary Examiner* — Robert R Raevis
(74) *Attorney, Agent, or Firm* — Brinks Hofer Gilson & Lione

(57) ABSTRACT

A specimen processing device comprising: first and second units for processing specimens; a conveyance unit for conveying a specimen rack in a first direction from a first position where the specimen is retrieved by the first unit to a second position where the specimen is retrieved by the second unit, and a second direction opposite to the first position; a detector common to the first and second units for executing a detection process with respect to the sample containers; and a conveyance controller controlling the conveyance unit to convey some sample containers of the detected sample containers executed with the detection process to the first position, and to convey the other sample containers of the detected sample containers to the second position, the some sample containers and the other sample containers being held by a common rack, is disclosed. A specimen processing method is also disclosed.

18 Claims, 26 Drawing Sheets

| HOLDING POSITION | PRESENCE OF SPECIMEN CONTAINER | MEASUREMENT ORDER | MEASUREMENT STATUS |
|---|---|---|---|
| 1 | 1 | CBC+DIFF | MEASURED |
| 2 | 0 | NULL | NULL |
| 3 | 1 | CBC+DIFF | MEASURED |
| 4 | 1 | CBC+DIFF, NRBC | MEASURED |
| 5 | 1 | CBC+DIFF | NOT MEASURED |
| 6 | 1 | CBC+DIFF, RET | NOT MEASURED |
| 7 | 1 | CBC+DIFF | NOT MEASURED |
| 8 | 1 | CBC+DIFF | NOT MEASURED |
| 9 | 0 | NULL | NULL |
| 10 | 0 | NULL | NULL |

FIG. 18A

| HOLDING POSITION (F1) | PRESENCE OF SPECIMEN CONTAINER (F2) | MEASUREMENT ORDER (F3) | MEASUREMENT STATUS (F4) |
|---|---|---|---|
| 1 | NULL | NULL | NULL |
| 2 | NULL | NULL | NULL |
| 3 | NULL | NULL | NULL |
| 4 | NULL | NULL | NULL |
| 5 | NULL | NULL | NULL |
| 6 | NULL | NULL | NULL |
| 7 | NULL | NULL | NULL |
| 8 | NULL | NULL | NULL |
| 9 | NULL | NULL | NULL |
| 10 | NULL | NULL | NULL |

FIG. 18B

| | F1 | F2 | F3 PT | F4 |
|---|---|---|---|---|
| | HOLDING POSITION | PRESENCE OF SPECIMEN CONTAINER | MEASUREMENT ORDER | MEASUREMENT STATUS |
| | 1 | 1 | CBC+DIFF | NOT MEASURED |
| | 2 | NULL | NULL | NULL |
| | 3 | NULL | NULL | NULL |
| | 4 | NULL | NULL | NULL |
| | 5 | NULL | NULL | NULL |
| | 6 | NULL | NULL | NULL |
| | 7 | NULL | NULL | NULL |
| | 8 | NULL | NULL | NULL |
| | 9 | NULL | NULL | NULL |
| | 10 | NULL | NULL | NULL |

FIG. 18F

| F1 | F2 | F3 | PT F4 |
|---|---|---|---|
| HOLDING POSITION | PRESENCE OF SPECIMEN CONTAINER | MEASUREMENT ORDER | MEASUREMENT STATUS |
| 1 | 1 | CBC+DIFF | DURING SPECIMEN RETRIEVAL (FIRST MEASUREMENT UNIT) |
| 2 | 1 | CBC+DIFF | DURING SPECIMEN RETRIEVAL (SECOND MEASUREMENT UNIT) |
| 3 | 1 | CBC+DIFF | NOT MEASURED |
| 4 | NULL | NULL | NULL |
| 5 | NULL | NULL | NULL |
| 6 | NULL | NULL | NULL |
| 7 | NULL | NULL | NULL |
| 8 | NULL | NULL | NULL |
| 9 | NULL | NULL | NULL |
| 10 | NULL | NULL | NULL |

SPECIMEN PROCESSING DEVICE AND SPECIMEN PROCESSING METHOD

RELATED APPLICATIONS

This application claims priority under 35 U.S.C. §119 to Japanese Patent Application Nos. 2009-112825 filed on May 7, 2009 and 2009-177821 filed on Jul. 30, 2009, the entire contents of which are hereby incorporated by reference.

FIELD OF THE INVENTION

The present invention relates to a specimen processing device including a specimen processing unit for processing a specimen, and a conveyance unit for conveying a specimen rack holding a plurality of specimen containers, and a specimen processing method executed in the specimen processing device.

BACKGROUND OF THE INVENTION

A specimen processing device including a plurality of measurement units, and a conveyance unit for conveying the specimen to the plurality of measurement units is conventionally known.

For instance, U.S. Pat. No. 5,209,903 discloses a total blood examination device including two blood analyzers, one smear producing device, and a conveyance device for conveying the specimen to such devices. The total blood examination device includes a barcode reader in each of the analyzer and the smear producing device, where whether or not the processing of specimen, by the device corresponding to the barcode reader that has performed reading, is necessary is determined according to the result of reading the barcode attached to the specimen container.

A specimen processing system configured to include a plurality of analyzing units, the system conveying the specimen rack to one of the analyzing units, and analyzing the specimen of each test tube held by the conveyed specimen rack with the analyzing unit at the conveyance destination is known. For instance, Japanese Laid-Open Patent Publication No. 11-316238 discloses an automatic analyzer including a plurality of analyzing units and a main conveyance line for conveying the specimen to the plurality of analyzing units. The automatic analyzer includes a barcode reader near the entrance of the main conveyance line, so that rack identification information and specimen ID are recognized by the barcode reader. The types of analyzing items that can be analyze processed by each analyzing unit are registered in a storage portion of a control unit arranged in the automatic analyzer, where with which one of the analyzing units to analyze process the specimen on the specimen rack is determined by the control unit with the recognition of the specimen ID. The automatic analyzer conveys the specimen rack to one analyzing unit with analyzing request, and the relevant analyzing unit analyzes the specimen of each test tube held at the specimen rack.

Japanese Laid-Open Patent Publication No. 2000-88860 discloses a specimen conveyance system in which a plurality of analyzers is connected from the upstream side to the downstream side with respect to the conveyance line for conveying the rack holding a plurality of specimens. In the specimen conveyance system disclosed in Japanese Laid-Open Patent Publication No. 2000-88860, a plurality of determination positions are set as positions immediately before each analyzer on the conveyance line, and a label reader is arranged at each determination position. The label reader can optically read the barcode label, that is, the rack label attached to the rack. A rack receiving portion is connected to the end on the upstream side of the conveyance line, the label reader is arranged at the exit side of the rack receiving portion, and the rack label and the label of each specimen are read by the label reader. The information read by the label reader arranged at the exit side of the rack receiving portion is sent to a scheduler, and the scheduler then acquires a list of analyzing items based on the rack ID and the specimen ID read by the label reader. The rack label is read by the label reader at each determination position, and the read information is sent to the scheduler. The scheduler determines to which analyzer to input the rack for every rack at each determination position in view of parameters such as the set analyzing item, the number of storage racks of the rack storage area in which the rack to be applied with the analyzer is stored, the total number of tests, the operation state, the availability state, and the processing ability for every analyzer, and performs the conveyance control of the rack so as to equalize the load in each analyzer.

However, in the total blood examination device disclosed in U.S. Pat. No. 5,209,903, the barcode reader needs to be arranged for each of the analyzer and the smear producing device, and hence the configuration is complicated.

In the automatic analyzer disclosed in Japanese Laid-Open Patent Publication No. 11-316238, the specimen of each test tube held by one specimen rack is analyzed by one analyzing unit, and hence the specimen cannot be efficiently processed.

In the specimen conveyance system disclosed in Japanese Laid-Open Patent Publication No. 2000-88860, a plurality of label readers needs to be arranged at the positions immediately before each analyzer to convey the rack to each analyzer, and hence the configuration is complicated. Furthermore, with respect to the same rack, the rack label needs to be read by the label reader arranged at each determination position after reading the rack ID and the specimen ID by the label reader arranged at the exit side of the rack receiving portion, and hence the number of reading by the label reader is great and the operation is wasteful.

SUMMARY OF THE INVENTION

The scope of the present invention is defined solely by the appended claims, and is not affected to any degree by the statements within this summary.

A first aspect of the present invention is a specimen processing device comprising: a first processing unit for processing a specimen; a second processing unit for processing a specimen; a conveyance unit for conveying a specimen rack in a first direction from a first position where the specimen is retrieved by the first processing unit to a second position where the specimen is retrieved by the second processing unit, and a second direction from the second position to the first position, the specimen rack holding a plurality of sample containers; a detector common to the first and second processing units for executing a predetermined detection process with respect to the sample containers held by the specimen rack; and a conveyance controller for controlling the conveyance unit to convey some sample containers of the detected sample containers executed with the detection process by the detector to the first position, and to convey the other sample containers of the detected sample containers to the second position, the some sample containers and the other sample containers being held by a common specimen rack.

A second aspect of the present invention is a specimen processing device comprising: a first processing unit for processing a specimen; a second processing unit for processing a specimen; an ID detector for detecting specimen identification information from a sample container; a conveyance unit for conveying a specimen rack to a first position where the specimen is retrieved by the first processing unit, a second position where the specimen is retrieved by the second processing unit, and a detection position where the specimen identification information is detected by the ID detector, the specimen rack holding a plurality of sample containers; and a conveyance controller for controlling the conveyance unit to convey a detected sample container executed with the detection by the ID detector to the first position if the first processing unit is not executing the specimen process, and to convey a non-detected sample container not executed with the detection by the ID detector to the detection position if the first and second processing units are executing the specimen process, the detected sample container and the non-detected sample container being held by a common specimen rack.

A third aspect of the present invention is a specimen processing method executed in a specimen processing device including a first processing unit for processing a specimen and a second processing unit for processing a specimen, the specimen processing method comprising: executing a predetermined detection process on a plurality of sample containers held by a specimen rack; conveying some sample containers of the detected sample containers executed with the detection process to a first position where the specimen is retrieved by the first processing unit; and conveying other sample containers of the detected sample containers to a second position where the specimen is retrieved by the second processing unit; wherein the some sample containers and the other sample containers are held by a common specimen rack.

A fourth aspect of the present invention is a specimen processing method executed in a specimen processing device including a first processing unit for processing a specimen and a second processing unit for processing a specimen, the specimen processing method comprising: executing a predetermined detection process on some of a plurality of sample containers held by a specimen rack; conveying a detected sample container executed with the detection process to a first position where the specimen is retrieved by the first processing unit if the first processing unit is not executing a specimen process; and conveying a non-detected sample container not executed with the detection process to a detection position if the first processing unit and the second processing unit are executing the specimen process; wherein the detected sample container and the non-detected sample container are held by a common specimen rack.

BRIEF DESCRIPTION OF THE DRAWINGS

FIG. 18A is a view schematically showing one example of a state of the specimen processing table;

FIG. 18B is a view schematically showing one example of a state of the specimen processing table;

FIG. 18F is a view schematically showing one example of a state of the specimen processing table.

DETAILED DESCRIPTION OF THE PREFERRED EMBODIMENTS

The preferred embodiment of the present invention will be described hereinafter with reference to the drawings.

The present embodiment relates to a specimen processing device, including a first measurement unit, a second measurement unit, a specimen conveyance unit, a barcode reader, a specimen container sensor, and an information processing unit, for conveying a sample rack holding a plurality of specimen containers with a specimen conveyance unit, detecting the presence of the specimen container with the specimen container sensor, and reading the specimen barcode with the barcode reader, and then conveying the sample rack with the specimen conveyance unit to allocate the plurality of specimen containers held by the sample rack to the first measurement unit and the second measurement unit.

[Configuration of Specimen Analyzer]

Figure 1A:
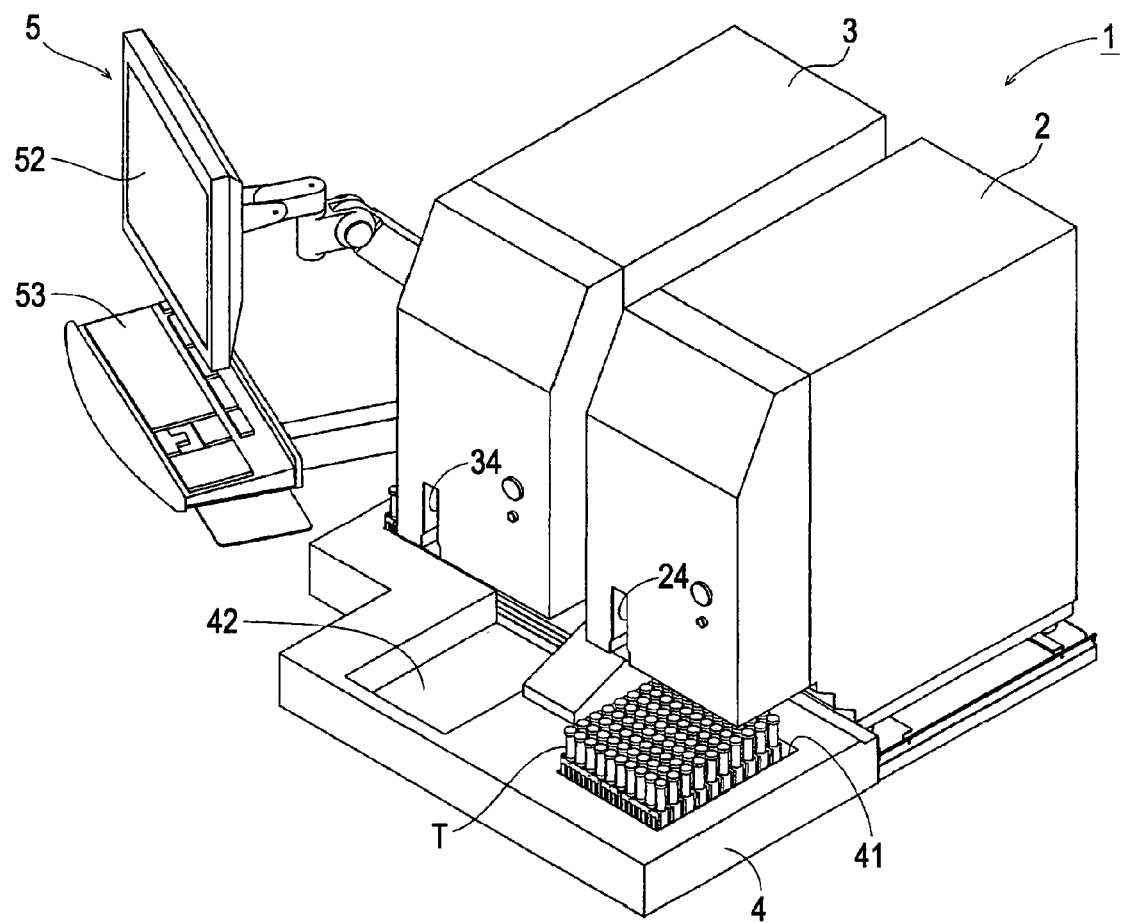
FIG. 1A is a perspective views showing an overall configuration of a specimen analyzer according to an embodiment.
Figure 1B:
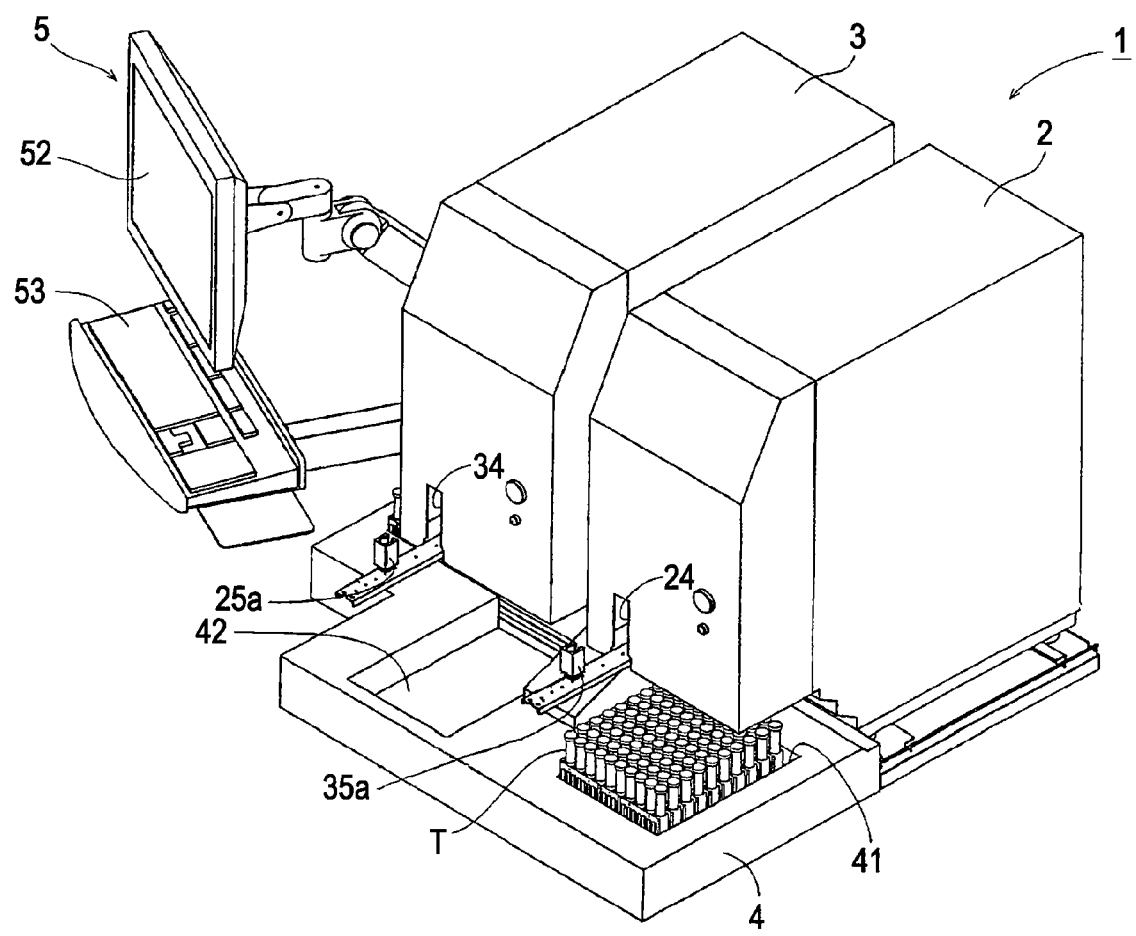
FIG. 1B is a perspective views showing an overall configuration of the specimen analyzer according to the embodiment.

FIGS. 1A and 1B are perspective views showing an overall configuration of the specimen analyzer according to the present embodiment. The specimen analyzer 1 according to the present embodiment is a multi-item blood cell analyzer for detecting the white blood cells, the red blood cells, the platelets, and the like contained in the blood specimen, and counting each blood cells. As shown in FIGS. 1A and 1B, the specimen analyzer 1 includes a first measurement unit 2, a second measurement unit 3, a specimen conveyance unit 4 arranged on the front surface side of the first measurement unit 2 and the second measurement unit 3, and an information processing unit 5 capable of controlling the first measurement unit 2, the second measurement unit 3, and the specimen conveyance unit 4.

Figure 2:
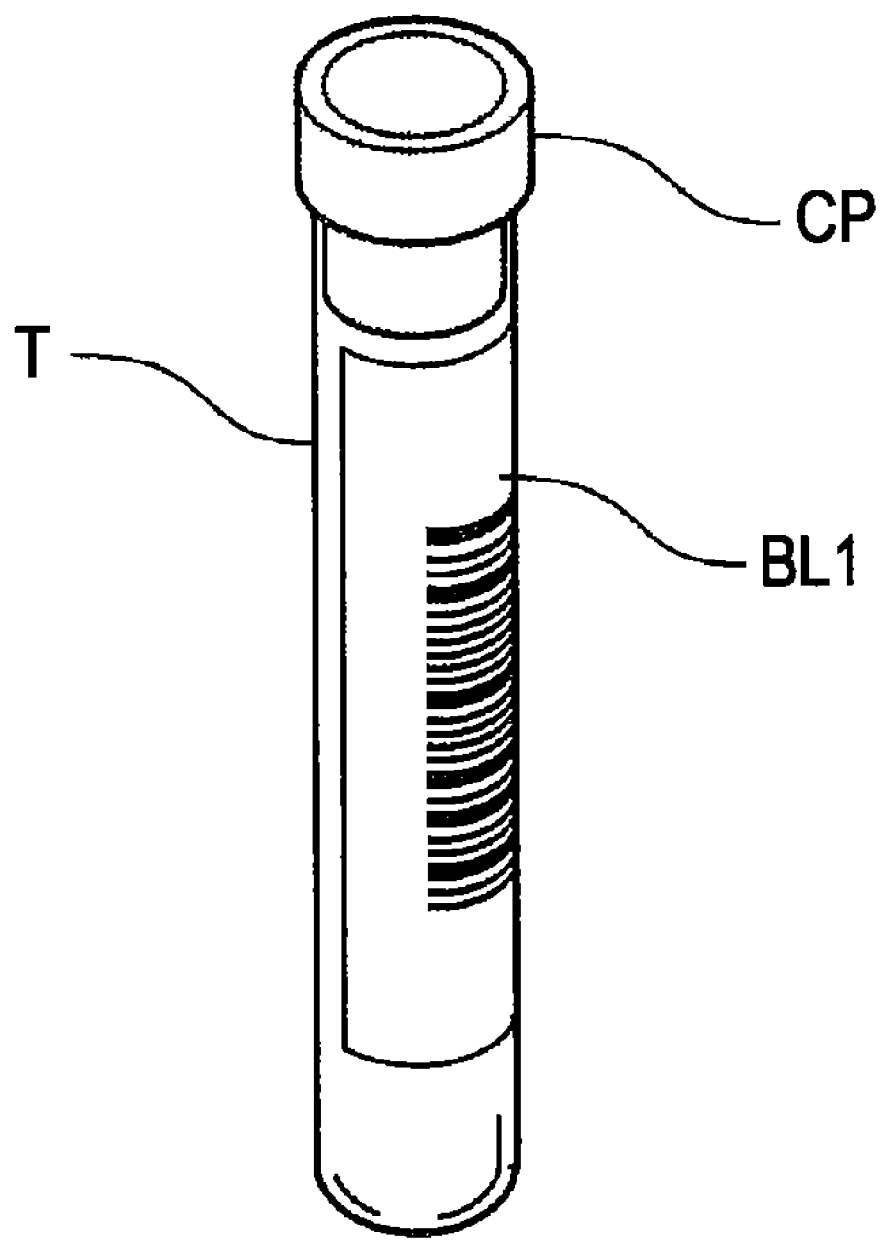
FIG. 2 is a perspective view showing an outer appearance of a specimen container.
Figure 3:
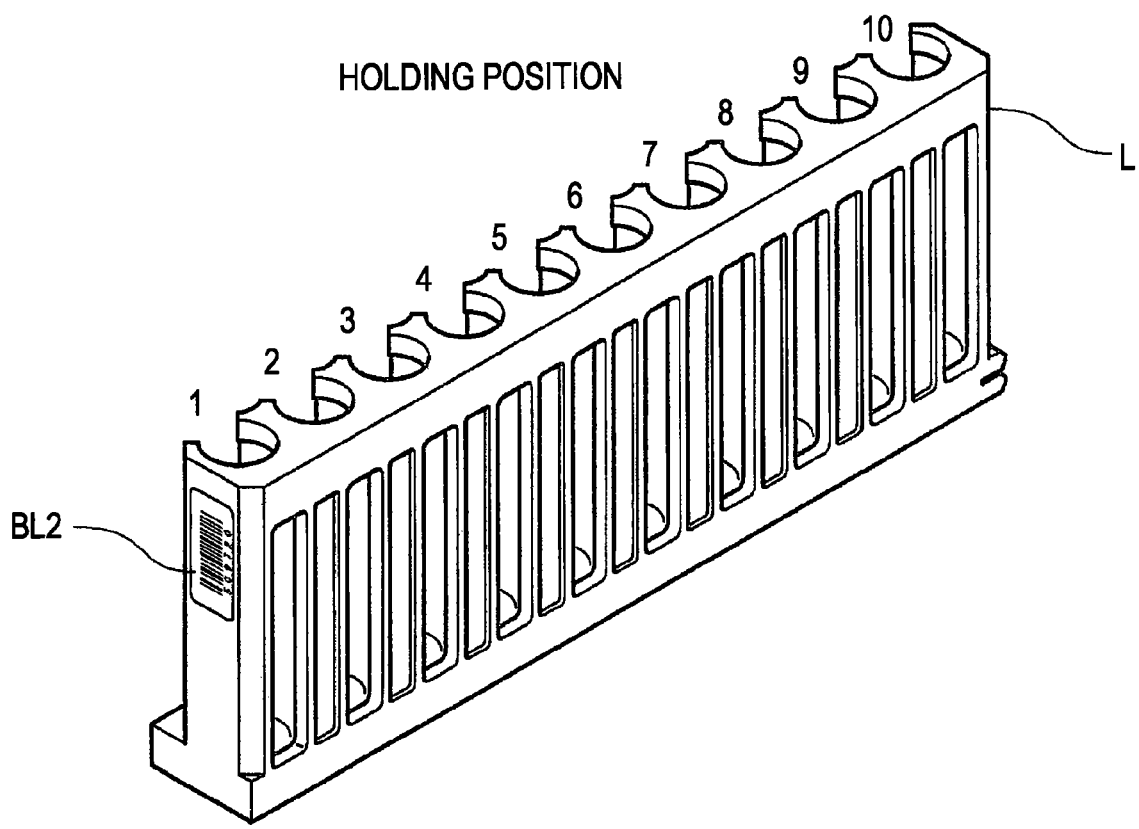
FIG. 3 is a perspective view showing an outer appearance of a sample rack.

FIG. 2 is a perspective view showing an outer appearance of a specimen container accommodating a specimen, and FIG. 3 is a perspective view showing an outer appearance of a sample rack for holding a plurality of specimen containers. As shown in FIG. 2, the specimen container T has a tubular shape, and the upper end thereof is opened. The blood specimen collected from a patient is accommodated therein, and the opening at the upper end is sealed by a lid CP. The specimen container T is made of a glass or a synthetic resin having translucency, so that the blood specimen inside can be seen. A barcode label BL1 is attached to the side surface of the specimen container T. A barcode indicating a specimen ID is printed on the barcode label BL1. As shown in FIG. 3, the sample rack L can hold ten specimen containers T side by side. Each specimen container T is held in a perpendicular state (standing state) in the sample rack L. A barcode label BL2 is attached to the side surface of the sample rack L. A barcode indicating a rack ID is printed on the barcode label BL2.

<Configuration of Measurement Unit>

Figure 4:
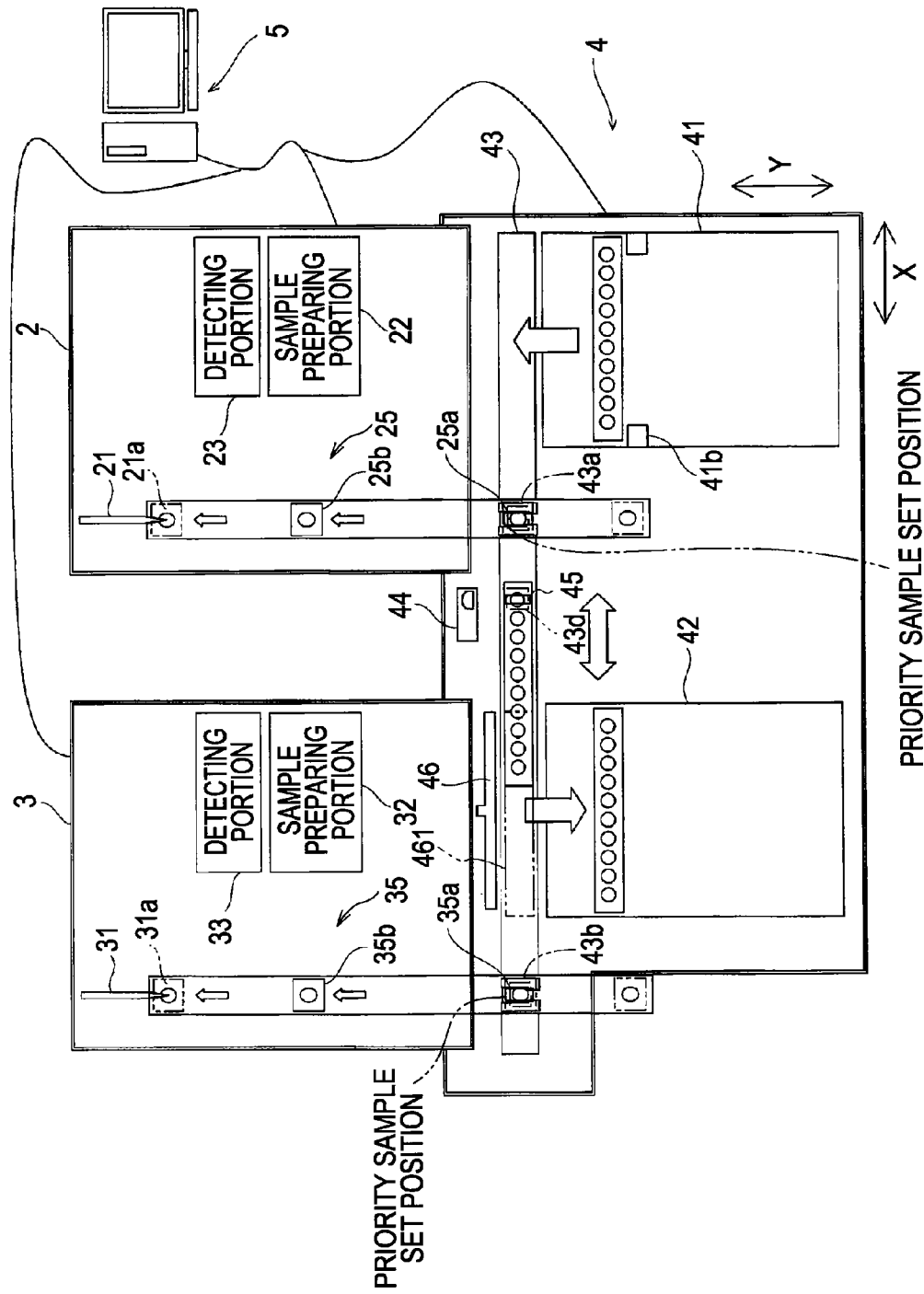
FIG. 4 is a block diagram showing a configuration of a measurement unit according to the embodiment.

The first measurement unit 2 is arranged on the upstream side in the conveyance direction (X-direction shown in FIG. 4) of the specimen of the specimen conveyance unit 4, and the second measurement unit 3 is arranged on the downstream side in the conveyance direction. FIG. 4 is a block diagram showing a configuration of the measurement unit. As shown in FIG. 4, the first measurement unit 2 includes a specimen aspirating portion 21 for aspirating the blood or the specimen from the specimen container (blood collecting tube) T, a sample preparing portion 22 for preparing a measurement sample used in the measurement from the blood aspirated by the specimen aspirating portion 21, and a detecting portion 23 for detecting the blood cell from the measurement sample prepared by the sample preparing portion 22. The first measurement unit 2 further includes a take-in port 24 (see FIGS. 1A and 1B) for taking in the specimen container T accommodated in the sample rack L conveyed by the rack conveyance portion 43 of the specimen conveyance unit 4 into the first measurement unit 2, and a specimen container conveyance portion 25 for taking in the specimen container T from the sample rack L into the first measurement unit 2 and conveying the specimen container T to the aspirating position by the specimen aspirating portion 21.

As shown in FIG. 4, an aspirating tube (not shown) is arranged at the distal end of the specimen aspirating portion 21. The specimen aspirating portion 21 is movable in the vertical direction, and is moved to the lower side so that the aspirating tube passes through the lid CP of the specimen container T conveyed to the aspirating position to aspirate the blood inside.

The sample preparing portion 22 includes a plurality of reaction chambers (not shown). The sample preparing portion 22 is connected to a reagent container (not shown), and can supply the reagent such as a stain reagent, a hemolyzing agent, and a diluted solution to the reaction chamber. The sample preparing portion 22 is also connected to the aspirating tube of the specimen aspirating portion 21, and can supply the blood specimen aspirated by the aspirating tube to the reaction chamber. Such sample preparing portion 22 mixes and stirs the specimen and the reagent in the reaction chamber, and prepares the sample for measurement (measurement sample) by the detecting portion 23.

The detecting portion 23 can perform the RBC (Red Blood Cell) detection and the PLT (Platelet) detection through the sheath flow DC detection method. In the detection of the RBC and the PLT by the sheath flow DC detection method, the measurement of the measurement sample, in which the specimen and the diluted solution are mixed, is performed, wherein the information processing unit 5 performs the analyzing process on the obtained measurement data to measure the RBC and the PLT. The detecting portion 23 can perform the HGB (Hemoglobin) detection through the SLS-hemoglobin method, and is configured to perform the detection of WBC (White Blood Cell), NEUT (Neutrophil Cell), LYMPH (Lymph Cell), EO (Eosinophil), BASO (Basophil) and MONO (Monocyte) through the flow cytometry method using the semiconductor laser. In the detecting portion 23, detecting methods differ for the detection of the WBC not involving the detection of five classification of the white blood cell, that is, the NEUT, the LYMPH, the EO, the BASO and the MONO, and for the detection of the WBC involving five classification of the white blood cell. In the detection of the WBC not involving five classification of the white blood cell, the measurement of the measurement sample, in which the specimen, the hemolyzing agent and the diluted solution are mixed, is performed, wherein the information processing unit 5 performs the analyzing process on the obtained measurement data to measure the WBC. On the other hand, in the detection of the WBC involving five classification of the white blood cell, the measurement of the measurement specimen, in which the stain reagent, the hemolyzing agent and the diluted solution are mixed, is performed, wherein the information processing unit 5 performs the analyzing process on the obtained measurement data to measure the NEUT, the LYMPH, the EO, the BASO, the MONO and the WBC.

The WBC, the RBC, the PLT, and the HGB are contained in the measurement items called the CBC item, and the WBC, the RBC, the PLT, the HGB, the NEUT, the LYMPH, the EO, the BASO, and the MONO are contained in the measurement items called the CBC+DIFF item. In the present embodiment, the CBC+DIFF item are measurement items commonly measurable with the first measurement unit 2 and the second measurement unit 3, and are basic items measured with respect to all specimens.

The detection unit 23 includes a flow cell (not shown), and has a configuration of detecting forward scattered light, lateral scattered light, and lateral fluorescent by sending the flow cell to a measurement sample and generating liquid flow in the flow cell, and irradiating the blood cells contained in the liquid flow passing through the flow cell with the semiconductor laser.

The light scattering is a phenomenon that occurs when a particle such as blood exists in the advancing direction of the light as an obstruction so that the light changes its advancing direction. Information related to size and material of the particle can be obtained by detecting the scattered light. In particular, information related to the size of the particle (blood cell) can be obtained from the forward scattered light. Information of the interior of the particle can be obtained from the lateral scattered light. When laser light is irradiated on the blood cell particle, the lateral scattered light intensity depends on the complexity of the interior of the cell (shape of core, size, density, amount of granulated powder). Therefore, the measurement of the classification of white blood cell, and other measurements can be performed using such a characteristic of the lateral scattered light intensity.

The configuration of the specimen container conveyance unit 25 will be described below. The specimen container conveyance portion 25 includes a hand portion 25a capable of gripping the specimen container T. The hand portion 25a includes a pair of gripping members arranged facing each other, and can approach or separate the gripping members to and from each other. The specimen container T can be gripped by approaching the relevant gripping members with the specimen container T in between. The specimen container conveyance portion 25 can move the hand portion 25a in the up and down direction and in the front and back direction (Y direction), and can oscillate the hand portion 25a. Thus, the specimen container T accommodated in the sample rack L and positioned at the first specimen supply position 43a can be gripped by the hand portion 25a, and the specimen container T can be taken out from the sample rack L by moving the hand portion 25a upward in the relevant state, and the specimen in the specimen container T can be stirred by oscillating the hand portion 25a.

The specimen container conveyance portion 25 includes a specimen container setting portion 25b with a hole for inserting the specimen container T. The specimen container T gripped by the hand portion 25a described above is moved after stirring is completed, and the gripped specimen container T is inserted to the hole of the specimen container setting portion 25b. Thereafter, the specimen container T is released from the hand portion 25a by separating the gripping members, and the specimen container T is set in the specimen container setting portion 25b. The relevant specimen container setting portion 25b is horizontally movable in the Y direction by the power of the stepping motor (not shown).

The specimen container setting portion 25b is movable to an aspirating position 21a by a specimen aspirating unit 21. When the specimen container setting portion 25b is moved to the aspirating position, the specimen is aspirated from the set specimen container T by the specimen aspirating portion 21.

The configuration of the second measurement unit 3 will now be described. The configuration of the second measurement unit 3 is the same as the configuration of the first measurement unit 2. The second measurement unit 3 includes a specimen aspirating portion 31, a sample preparing portion 32 for preparing a measurement sample used in the measurement from the blood aspirated by the specimen aspirating portion 31, and a detecting portion 33 for detecting the blood cell from the measurement sample prepared by the sample preparing portion 32. The second measurement unit 3 further includes a take-in port 34 (see FIGS. 1A and 1B) for taking in the specimen container T accommodated in the sample rack L conveyed by the rack conveyance portion 43 of the specimen conveyance unit 4 into the second measurement unit 3, and a specimen container conveyance portion 35 for taking in the specimen container T from the sample rack L into the second measurement unit 3 and conveying the specimen container T to the aspirating position by the specimen aspirating portion 31. The configurations of the specimen aspirating portion 31, the sample preparing portion 32, the detecting portion 33, the take-in port 34, and the specimen container conveyance portion 35 are similar to the configurations of the specimen aspirating portion 21, the sample preparing portion 22, the detecting portion 23, the take-in port 24, and the specimen container conveyance portion 25, and thus the description thereof will be omitted.

Similar to the first measurement unit 2, the second measurement unit 3 can measure the specimen for each measurement item of the WBC, the RBC, the PLT, the HGB, the NEUT, the LYMPH, the EO, the BASO, and the MONO, which are the CBC+DIFF items. The configuration of the second measurement unit 3 is similar to the configuration of the first measurement unit, and thus the description thereof will be omitted.

The first measurement unit 2 and the second measurement unit 3 can retrieve inside the specimen container T accommodating another specimen while measuring the measurement sample prepared from one specimen with the detection units 22, 32.

<Configuration of Specimen Conveyance Unit>

The configuration of the specimen conveyance unit 4 will now be described. As shown in FIGS. 1A and 1B, the specimen conveyance unit 4 is arranged on the front side of the first measurement unit 2 and the second measurement unit 3 of the specimen analyzer 1. Such a specimen conveyance unit 4 can convey the sample rack L to supply the specimen to the first measurement unit 2 and the second measurement unit 3.

Figure 5:
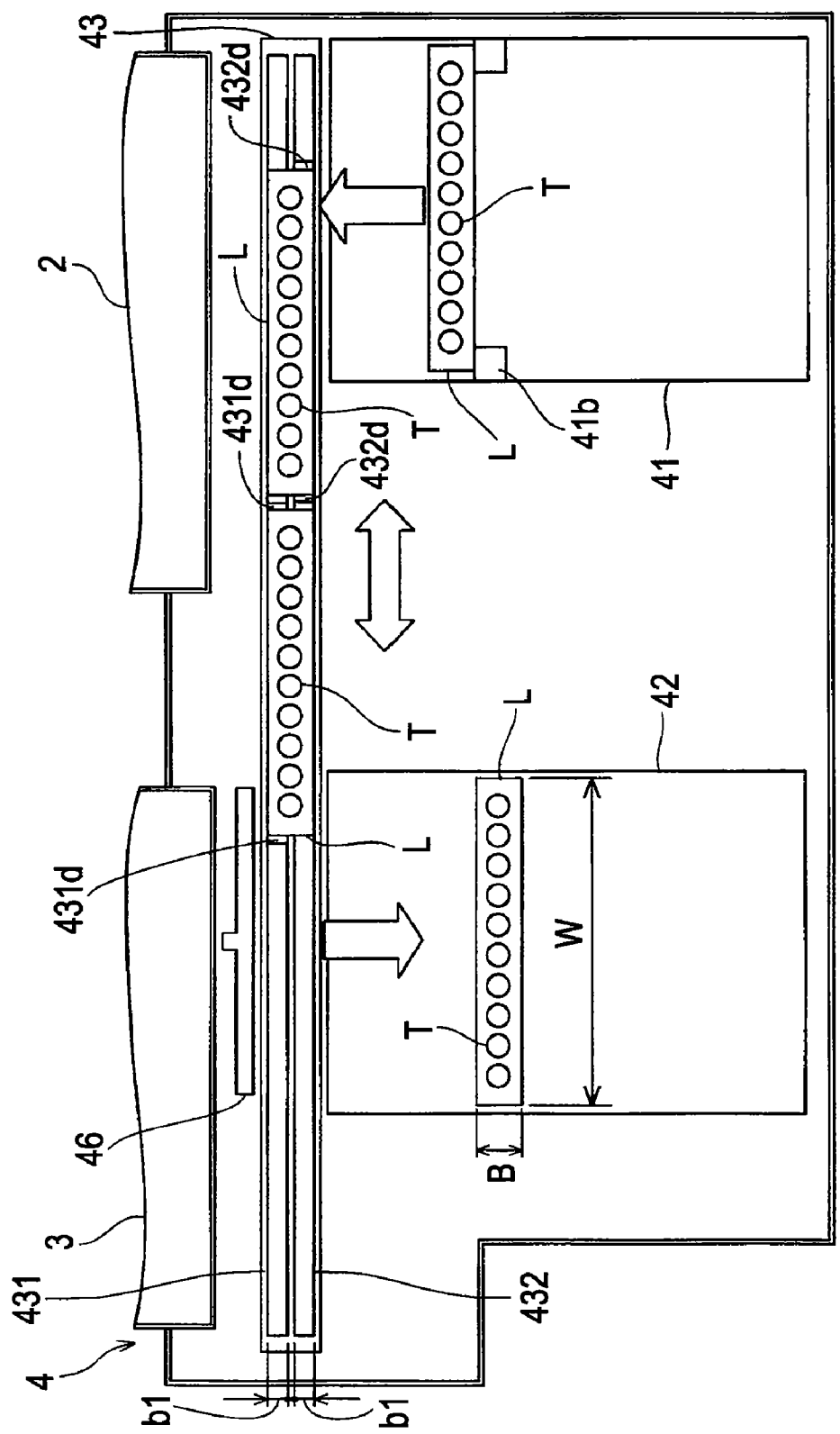
FIG. 5 is a plan view showing a configuration of the specimen conveyance unit.

FIG. 5 is a plan view showing a configuration of the specimen conveyance unit 4. As shown in FIG. 5, the specimen conveyance unit 4 includes a pre-analysis rack holder 41 capable of temporarily holding a plurality of sample racks L for holding the specimen container T accommodating the specimen before the analysis, a post-analysis rack holder 42 capable of temporarily holding a plurality of sample racks L for holding the specimen container T from which the specimen is aspirated by the first measurement unit 2 or the second measurement unit 3, a rack conveyance portion 43 for moving the sample rack L horizontally and linearly in the direction of the arrow X in the figure to supply the specimen to the first measurement unit 2 or the second measurement unit 3, and conveying the sample rack L received from the pre-analysis rack holder 41 to the post-analysis rack holder 42, a barcode reading unit 44 (see FIG. 4), and a specimen container sensor 45 for detecting the presence of the specimen container (see FIG. 4).

The pre-analysis rack holder 41 has a square shape in plan view, which width is slightly larger than the width of the sample rack L. The pre-analysis rack holder 41 is formed to be one step lower than the peripheral surface, so that the sample rack L before the analysis is mounted on the upper surface thereof. A rack send-in portion 41b is arranged projecting towards the inner side from both side surfaces of the pre-analysis rack holder 41. The rack send-in portion 41b engages with the sample rack L by projecting out, and the sample rack L is moved to the back side when moved to the back side in such a state (direction of approaching the rack conveyance portion 43). Such a rack send-in portion 41b is configured to be drivable by a stepping motor (not shown) arranged on the lower side of the pre-analysis rack holder 41.

As shown in FIG. 5, the rack conveyance portion 43 can move the sample rack L moved by the pre-analysis rack holder 41 to the X direction. A first specimen supply position 43a for supplying the specimen to the first measurement unit 2 and a second specimen supply position 43b for supplying the specimen to the second measurement unit 3 shown in FIG. 4 are provided on the conveyance path of the sample rack L by the rack conveyance portion 43. Returning back to FIG. 4, the specimen conveyance unit 4 is controlled by the information processing unit 5, and grips the specimen container T conveyed by the hand portion 25a or 35a of the corresponding measurement unit and takes out the specimen container T from the sample rack L to supply the specimen to the first measurement unit 2 or the second measurement unit 3 when conveying the specimen to the first specimen supply position 43*a* or the second specimen supply position 43*b*. The hand portion 25*a* or 35*a* gripping the specimen container T thereby enters the housing of the first measurement unit 2 or the second measurement unit 3, so that the specimen is retrieved into the first measurement unit 2 or the second measurement unit 3. The rack conveyance unit 43 can convey the sample rack L even while the specimen is being retrieved to the first measurement unit 2 or the second measurement unit 3. Therefore, while one of the first measurement unit 2 and the second measurement unit 3 is retrieving the specimen, the specimen cannot be retrieved to the relevant measurement unit, and hence the sample rack L is conveyed to another measurement unit to retrieve the specimen.

Figure 6:
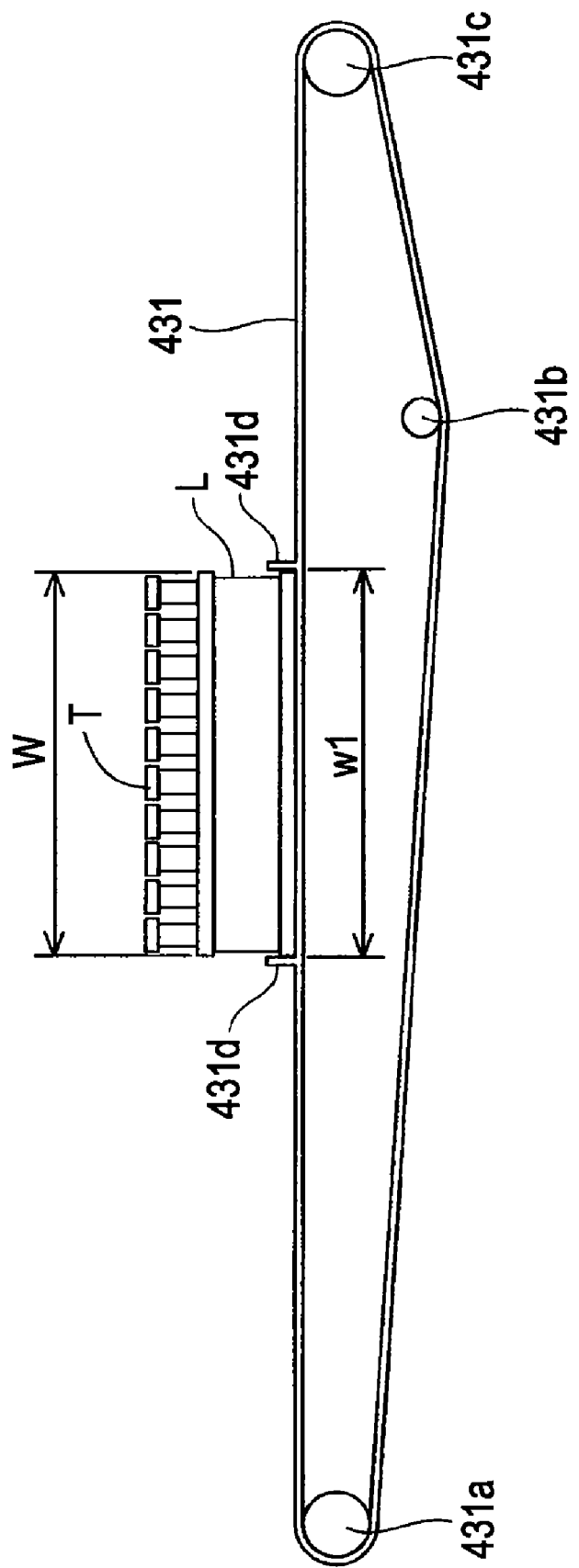
FIG. 6 is a front view showing a configuration of a first belt of the specimen conveyance unit.
Figure 7:
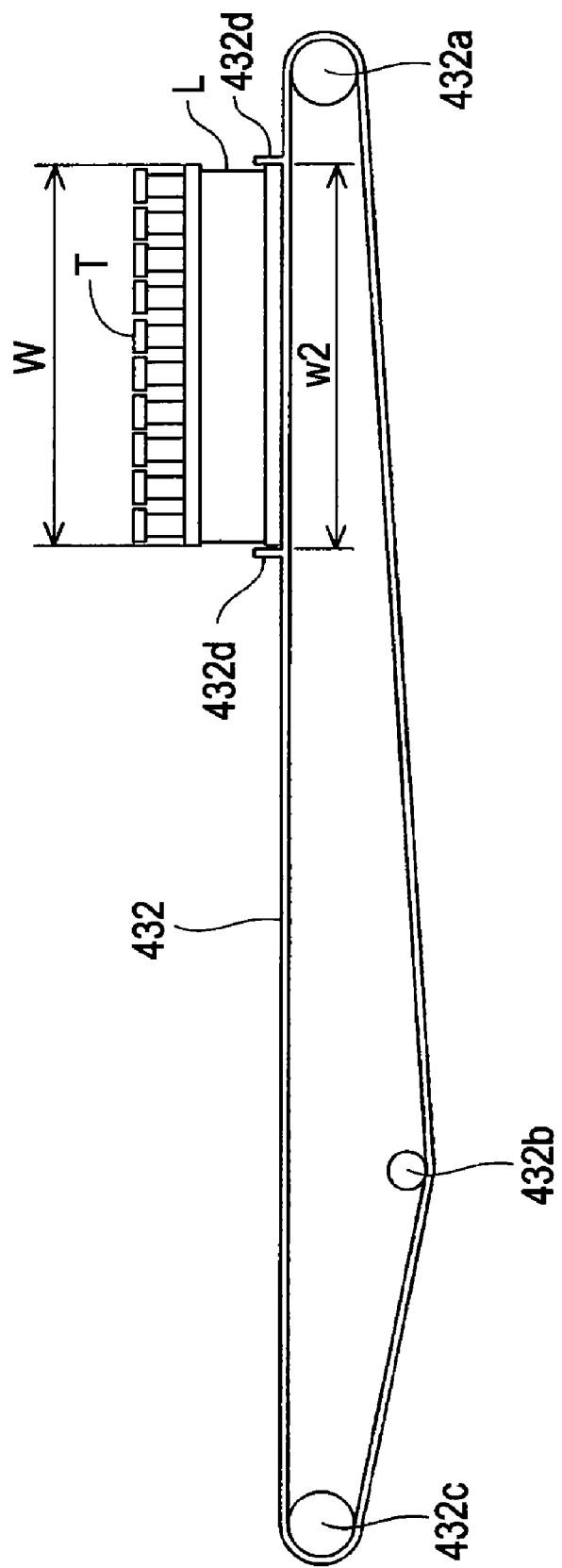
FIG. 7 is a front view showing a configuration of a second belt of the specimen conveyance unit.

The configuration of the rack conveyance unit 43 will be described in detail with reference to FIGS. 5 to 7. As shown in FIG. 5, the rack conveyance portion 43 includes two belts, a first belt 431 and a second belt 432, which are independently operable. The width b1 in the direction of the arrow Y of the first belt 431 and the second belt 432 is the size of smaller than or equal to half of the width B in the direction of the arrow Y of the sample rack L. Such first belt 431 and second belt 432 are arranged in parallel so as not to run out from the width B of the sample rack L when the rack conveyance portion 43 conveys the sample rack L. FIG. 6 is a front view showing a configuration of the first belt 431, and FIG. 7 is a front view showing a configuration of the second belt 432. As shown in FIGS. 6 and 7, the first belt 431 and the second belt 432 are formed to an annular shape, wherein the first belt 431 is arranged to surround rollers 431*a* to 431*c* and the second belt 432 is arranged to surround rollers 432*a* to 432*c*. Two projecting pieces 431*d* having an inner width w1 slightly (e.g., 1 mm) larger than the width W in the X direction of the sample rack L are arranged on the outer peripheral part of the first belt 431, and similarly, as shown in FIG. 7, two projecting pieces 432*d* having an inner width w2 of the same extent as the inner width w1 are arranged on the outer peripheral part of the second belt 432. The first belt 431 is configured to move the sample rack L in the direction of the arrow X by being moved at the outer periphery of the rollers 431*a* to 431*c* by the stepping motor (not shown) while holding the sample rack L on the inner side of the two projecting pieces 431*d*. The second belt 432 is configured to move the sample rack L in the direction of the arrow X by being moved at the outer periphery of the rollers 432*a* to 432*c* by the stepping motor (not shown) while holding the sample rack L on the inner side of the two projecting pieces 432*d*. The first belt 431 and the second belt 432 are also configured to move the sample rack L independently of each other. The rack conveyance unit 43 can convey the sample rack L so that the specimen is conveyed up to the first specimen supply position 43*a*, the second specimen supply position 43*b*, and a reading position 43*d* at which the barcode reading unit 44 reads the barcode printed on the barcode label BL1 of the specimen container T.

Returning back to FIG. 4, the barcode reading unit 44 is configured to read the barcode printed on the barcode label BL1 of the specimen container T shown in FIG. 5, and read the barcode printed on the barcode label BL2 attached to the sample rack L. The barcode reading unit 44 is configured to read the barcode of the specimen container T while rotating the target specimen container T by a rotation device (not shown) while accommodated in the sample rack L. The barcode thus can be directed to the barcode reading unit 44 side by rotating the specimen container T even if the barcode of the specimen container T is attached to the opposite side with respect to the barcode reading unit 44. The barcode printed in the barcode label BL2 of the sample rack L is uniquely attached to each rack, and used for the management etc. of the analysis result of the specimen. The barcode reading position 43*d* is provided between the first specimen supply position 43*a* and the second specimen supply position 43*b* on the conveyance path of the sample rack L by the rack conveyance unit 43, and the barcode reading unit 44 is arranged near the barcode reading position 43*d*. The barcode reading unit 44 can read the specimen barcode of the specimen container T positioned at the barcode reading position 43*d*.

The specimen container sensor 45 is a contact-type sensor, and includes a curtain-shaped contact piece, a light emitting element for emitting light, and a light receiving element (not shown). The specimen container sensor 45 is configured such that the contact piece is bent by contacting the detecting object of the detection target, and as a result, the light emitted from the light emitting element is reflected by the contact piece and received by the light receiving element. Therefore, when the specimen container T of the detection target accommodated in the sample rack L passes below the specimen container sensor 45, the contact piece is bent by the specimen container T, and the specimen container T is detected. The specimen container sensor 45 is arranged at the barcode reading position 43*d*. The presence of the specimen container T at the barcode reading position 43*d* can be detected by the specimen container sensor 45.

A post-analysis rack holder 42, to be described later, is arranged at the downstream side end in the conveyance direction of the rack conveyance unit 43, and a rack sending unit 46 is arranged at the back side of the post-analysis rack holder 42. The rack sending portion 46 is configured to move horizontally and linearly in the direction of the arrow Y by the driving force of the stepping motor (not shown). Thus, when the sample rack L is conveyed to a position 461 (hereinafter referred to as "post-analysis rack sending position") between the post-analysis rack holder 42 and the rack sending portion 46, the rack sending portion 46 is moved to the post-analysis rack holder 42 side so that the sample rack L can be pushed and moved into the post-analysis rack holder 42.

The post-analysis rack holder 42 has a square shape in a plan view, which width is slightly larger than the width of the sample rack L. The post-analysis rack holder 42 is formed to be one step lower than the peripheral surface so that the sample rack L, which analysis is completed, is mounted on the upper surface thereof. The post-analysis rack holder 42 is connected to the rack conveyance portion 43, so that the sample rack L is sent from the rack conveyance portion 43 by the rack sending portion 46.

With such a configuration, the specimen conveyance unit 4 transfers the sample rack L mounted on the pre-analysis rack holder 41 to the rack conveyance unit 43, conveys the specimen to the barcode reading position 43*d* by the rack conveyance unit 43, performs detection of the presence of the specimen container and the reading (detection) of the specimen ID, conveys the specimen from which the specimen ID is read to the first specimen supply position 43*a* or the second specimen supply position 43*b*, and supplies the same to the first measurement unit 2 or the second measurement unit 3. The sample rack L accommodating the specimen, which aspiration is completed, is moved to the post-analysis rack sending position 461 by the rack conveyance portion 43, and sent to the post-analysis rack holder 42 by the rack sending portion 46. If a plurality of sample racks L are mounted on the pre-analysis rack holder 41, the sample rack L accommodating the specimen, which analysis is completed, is sequentially sent to the post-analysis rack holder 42 by the rack sending portion 46, and such a sample racks L are stored in the post-analysis rack holder 42.

<Configuration of Information Processing Unit>

Figure 8:
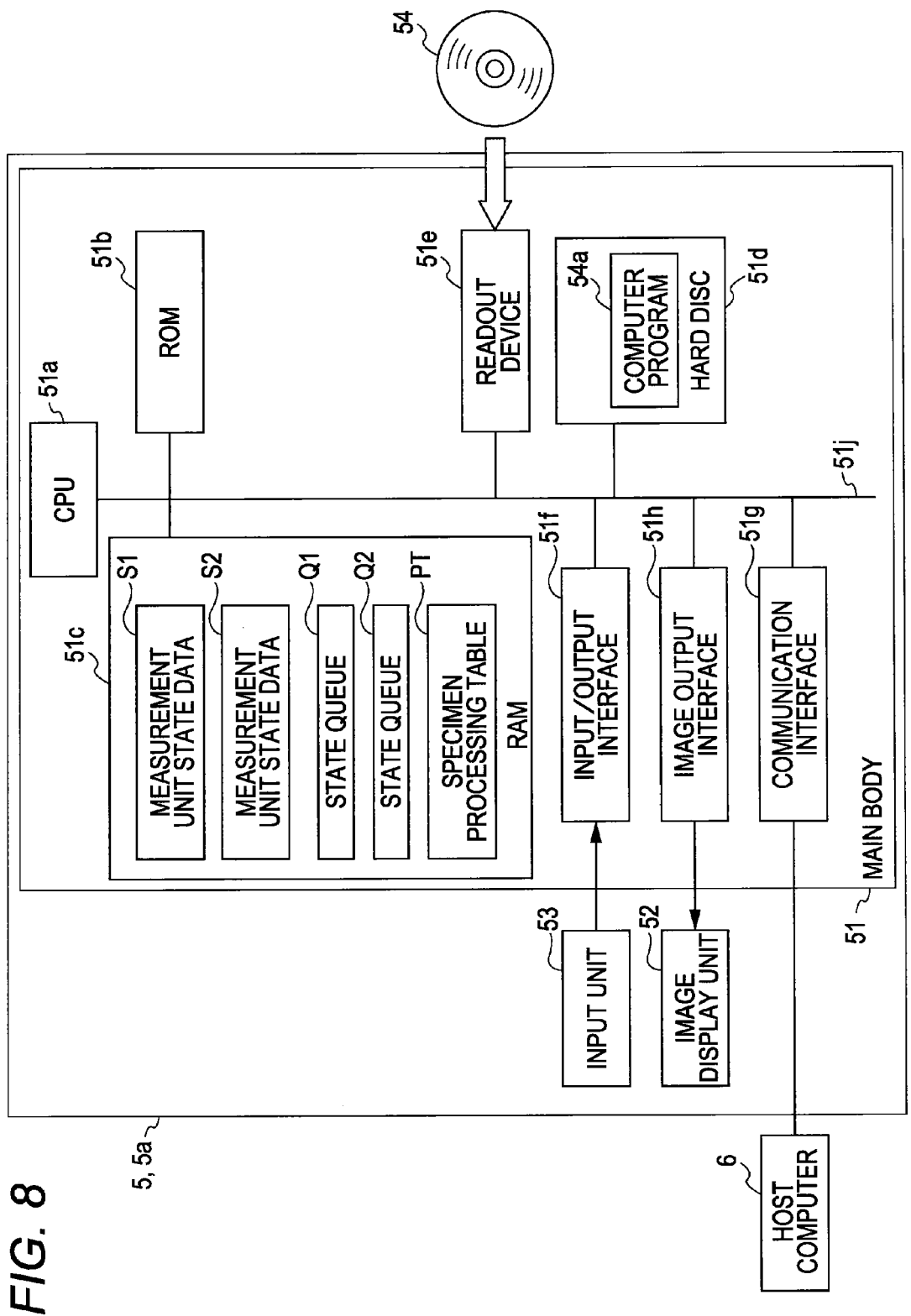
FIG. 8 is a block diagram showing a configuration of an information processing unit according to the embodiment.

The configuration of the information processing unit 5 will now be descried. The information processing unit 5 is configured by a computer. FIG. 8 is a block diagram showing the configuration of the information processing unit 5. The information processing unit 5 is realized by a computer 5a. As shown in FIG. 8, the computer 5a includes a main body 51, an image display unit 52, and an input unit 53. The main body 51 includes a CPU 51a, a ROM 521b, a RAM 51c, a hard disc 51d, a readout device 51e, an input/output interface 51f, a communication interface 51g, and an image output interface 51h, wherein the CPU 51a, the ROM 51b, the RAM 51c, the hard disc 51d, the readout device 51e, the input/output interface 51f, the communication interface 51g, and the image output interface 51h are connected by a bus 51j.

The CPU 51a can execute the computer program loaded in the RAM 51c. The computer 5a functions as the information processing unit 5 when the CPU 51a executes a computer program 54a for specimen analysis and for control of the first measurement unit 2, the second measurement unit 3, and the specimen conveyance unit 4, to be hereinafter described.

The ROM 51b is configured by mask ROM, PROM, EPROM, EEPROM, and the like, and is recorded with the computer program executed by the CPU 51a, the data used when executing the computer program, and the like.

The RAM 51c is configured by SRAM, DRAM, or the like. The RAM 51c is used to read out the computer program 54a recorded in the hard disc 51d. The RAM 51c is used as a work region of the CPU 51a when the CPU 51a executes such computer programs.

The RAM 51c includes measurement unit state data regions S1 and S2 indicating the states of the first measurement unit 2 and the second measurement unit 3, respectively. The measurement unit state data regions S1, S2 hold the data of one of "specimen retrievable", "specimen unretrievable/unreturnable", and "specimen returnable". When in the standby state in which measurement unit is not performing retrieval and measurement of the specimen, and waiting for the retrieval of the specimen, the state of the measurement unit is "specimen retrievable". When the measurement unit is performing the retrieval of the specimen, the state of the measurement unit is "specimen unretrievable/unreturnable". Furthermore, when in the state in which the aspiration of the specimen retrieved by the measurement unit is terminated and waiting for the returning of the specimen container T to the sample rack L, the state of the measurement unit is "specimen returnable". The measurement unit measures the measurement sample by the detection units 23, 33 (i.e., detects the blood cells), where after the returning of the specimen container T is completed, the state of the measurement unit becomes "specimen retrievable" in which new specimen can be retrieved.

The RAM 51c includes regions of state queues Q1 and Q2 for storing the state data of the first measurement unit 2 and the second measurement unit 3. The relevant state queues Q1 and Q2 accept the state data of the first measurement unit 2 and the second measurement unit 3 in real time, and hold the state data in a list structure of first in first out type.

The hard disc 51d is installed with various computer programs to be executed by the CPU 51a, and the data used for the execution of the computer program, such as an operating system and an application program. The computer program 54a to be hereinafter described is also installed in the hard disc 51d.

The readout device 51e is configured by flexible disc drive, CD-ROM drive, DVD-ROM, or the like. The readout device 51e can read out computer program or data recorded in a portable recording medium 54. The portable recording medium 54 stores the computer program 54a for causing the computer to function as the information processing unit 5, wherein the computer 5a reads out the computer program 54a from the portable recording medium 54, and installs the computer program 54a in the hard disc 51d.

The computer program 54a is not limited to being provided by the portable recording medium 54, and may be provided through an electrical communication line from an external device communicably connected to the computer 5a by the electrical communication line (wired or wireless). For instance, the computer program 54a may be stored in a hard disc of a server computer on the Internet, and the computer 5a may access the server computer, and download the computer program and store the same in the hard disc 51d.

The hard disc 51d is installed with a multi-task operating system such as Windows (registered trademark) manufactured and sold by US Microsoft Co. In the following description, the computer program 54a according to the present embodiment is assumed to operate on the operating system.

The input/output interface 51f is configured by serial interface such as USB, IEEE1394, RS-232C; parallel interface such as SCSI, IDE, IEEE1284; analog interface including D/A converter, A/D converter and the like. The input/output interface 51f is connected with the input unit 53 such as a keyboard and a mouse, and the user can input data to the computer 5a by using the input unit 53. The input/output interface 51f is connected to the first measurement unit 2, the second measurement unit 3, and the specimen conveyance unit 4. The information processing unit 5 thus can control the first measurement unit 2, the second measurement unit 3, and the specimen conveyance unit 4.

The communication interface 51g is an Ethernet (registered trademark) interface. The communication interface 51g is connected to a host computer 6 through the LAN. The computer 5a can transmit and receive data with the host computer 6 connected to the LAN using a predetermined communication protocol by the communication interface 51g.

The image output interface 51h is connected to the image display unit 52 configured by LCD, CRT, or the like, and outputs a video signal corresponding to the image data provided from the CPU 51a to the image display unit 52. The image display unit 52 displays an image (screen) according to the input video signal.

[Operation of Specimen Analyzer 1]

The operation of the specimen analyzer 1 according to the present embodiment will be described below.

<Description of Basic Operation of Specimen Processing Device 1>

Figure 9:
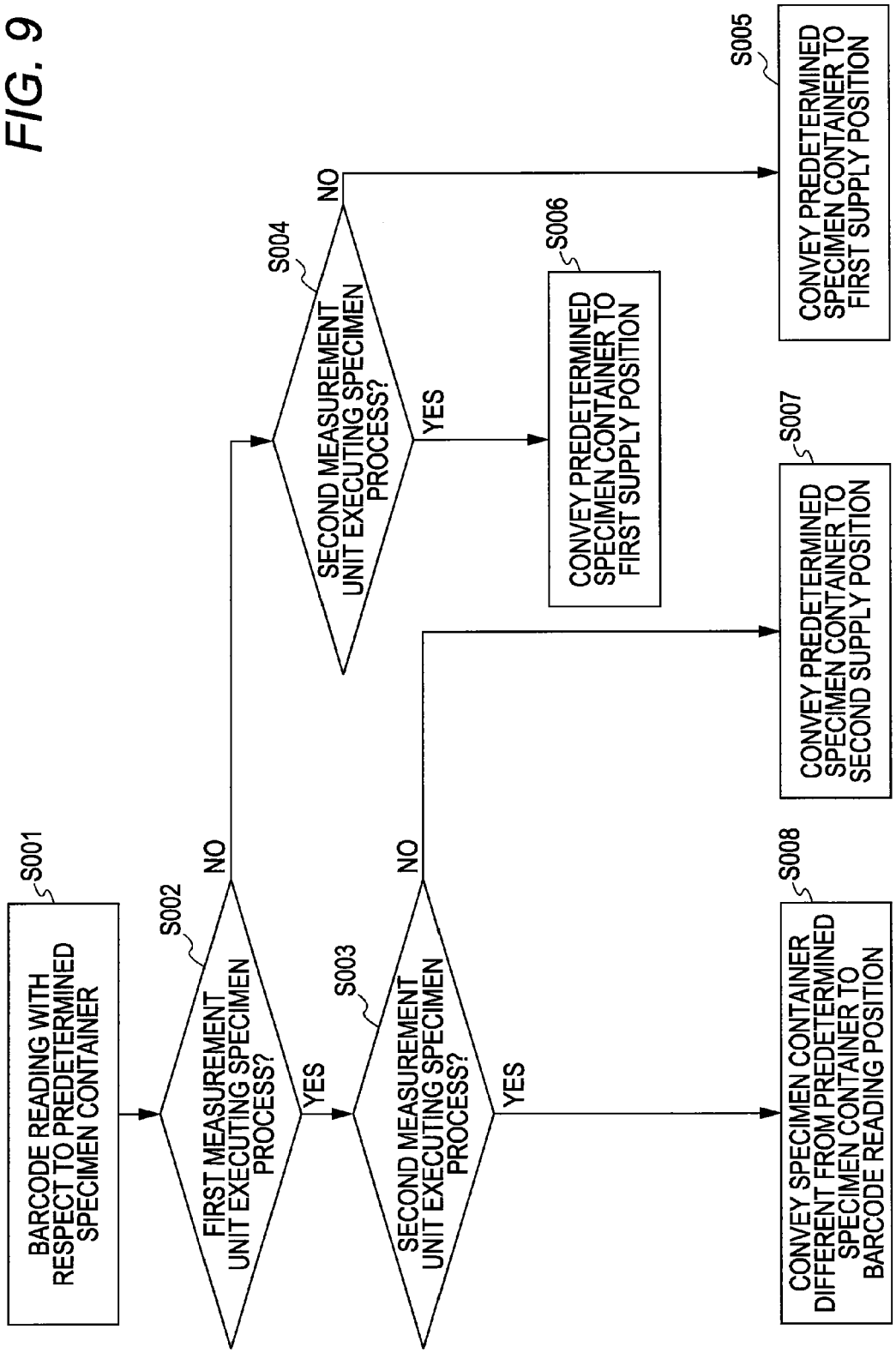
FIG. 9 is a flowchart describing the flow of the basic operation from the reading of the specimen barcode up to the conveyance of the sample rack by the specimen processing device according to the present embodiment.

First, the description of the basic operation of the specimen processing device 1 according to the present embodiment will be made. FIG. 9 is a flowchart describing the flow of the basic operation from the reading of the specimen barcode up to the conveyance of the sample rack L by the specimen processing device 1 according to the present embodiment. The sample rack L holds one to ten specimen containers T. The specimen processing device 1 performs the reading of the specimen barcode with respect to a predetermined specimen container T held by the sample rack L (step S001), and determines whether or not the first measurement unit 2 and the second measurement unit 3 are performing the retrieval of the specimen container T, the stirring of the specimen, the aspiration of the specimen from the specimen container T, and the return of the specimen container T (specimen process) (steps S002, S003, S004). If the first measurement unit 2 and the second measurement unit 3 are not performing the specimen process (NO in steps S002 and S004), the specimen processing device 1 conveys the predetermined specimen container T to the first supply position 43a to measure the specimen accommodated in the predetermined specimen container T in the first measurement unit 2 (step S005).

If the first measurement unit 2 is not executing the specimen process (NO in step S002), and the second measurement unit 3 is executing the specimen process (YES in step S004), the specimen processing device 1 conveys the predetermined specimen container T to the first supply position 43a to measure the specimen accommodated in the predetermined specimen container T in the first measurement unit 2 (step S006).

If the first measurement unit 2 is executing the specimen process (YES in step S502), and the second measurement unit 3 is not executing the specimen process (NO in step S003), the specimen processing device 1 conveys the predetermined specimen container T to the second supply position 43b to measure the specimen accommodated in the predetermined specimen container T in the second measurement unit 3 (step S007).

Furthermore, if the first measurement unit 2 and the second measurement unit 3 are both performing the specimen process (YES in steps S002 and S003), the specimen processing device 1 conveys the specimen container T held at the holding position different from the predetermined specimen container T to the barcode reading position 43d to execute the reading of the specimen barcode with respect to the specimen container T different from the predetermined specimen container T, that is, the specimen container T held at the holding position different from the predetermined specimen container T in the sample rack L (step S008).

The operation of the specimen processing device 1 will be more specifically described below.

<Specimen Conveyance Control Process>

Figure 10A:
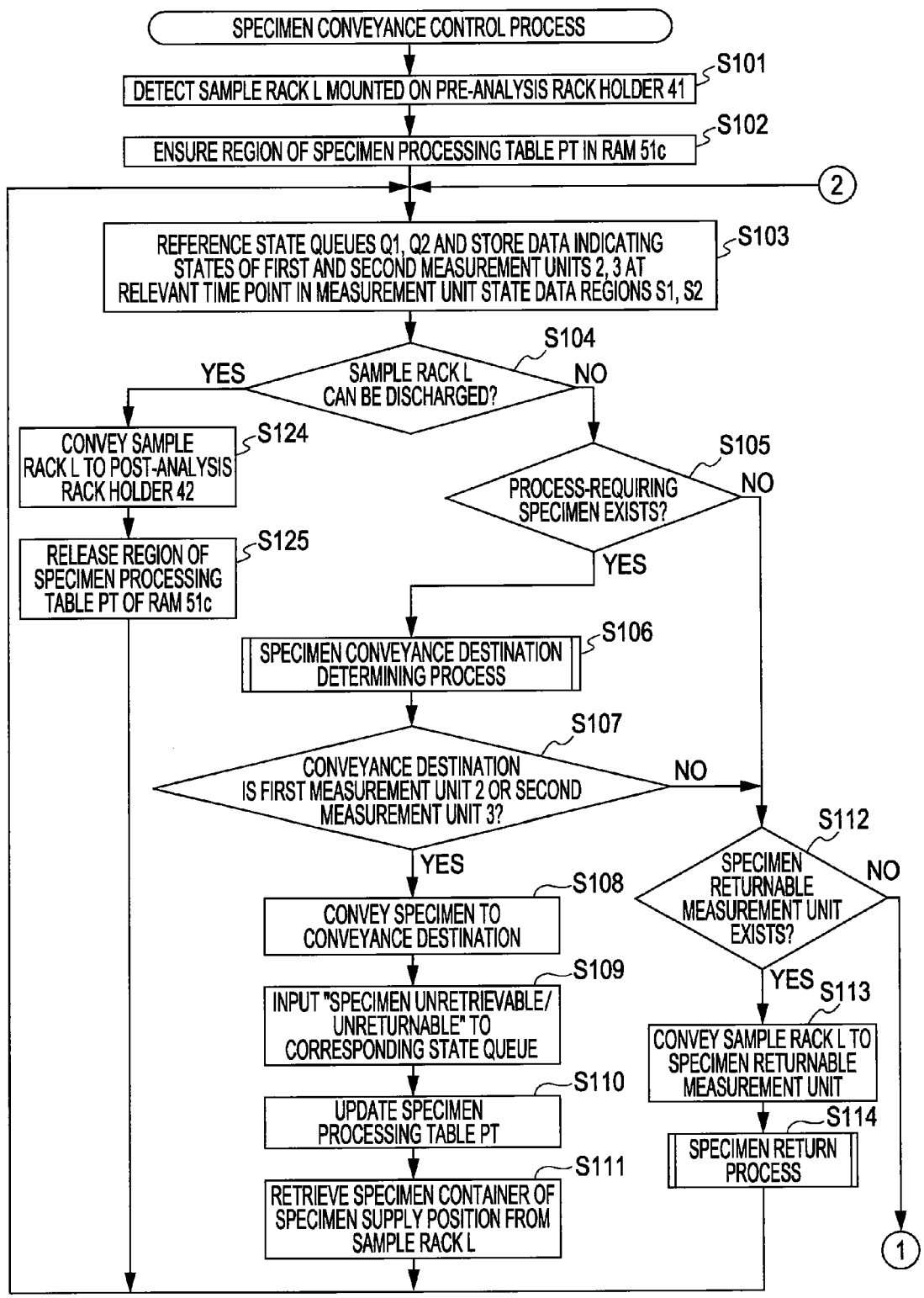
FIG. 10A is a flowchart showing a flow of the specimen conveyance control process by the CPU of the information processing unit of the specimen processing device.
Figure 10B:
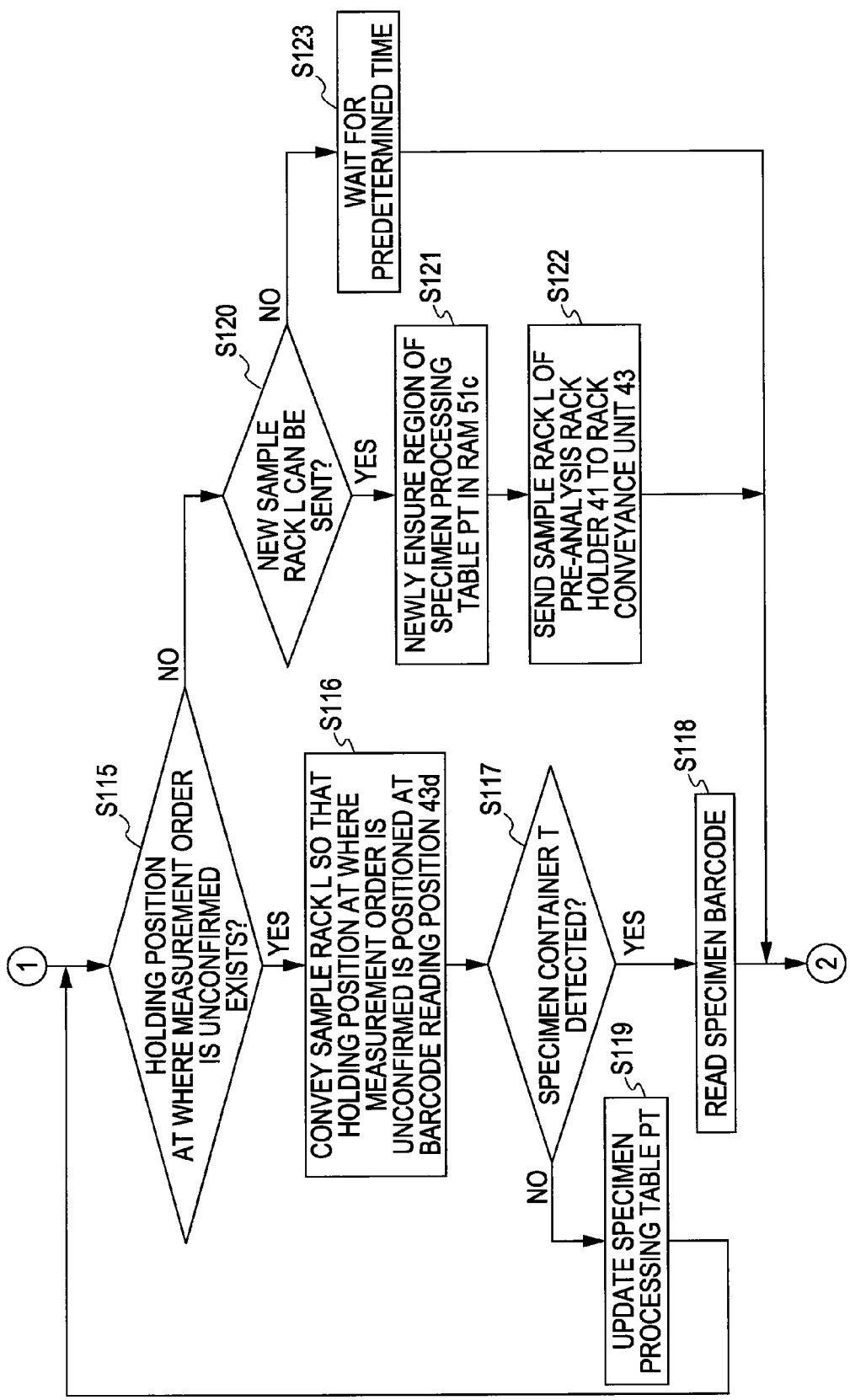
FIG. 10B is a flowchart showing a flow of the specimen conveyance control process by the CPU of the information processing unit of the specimen processing device.
Figure 11:
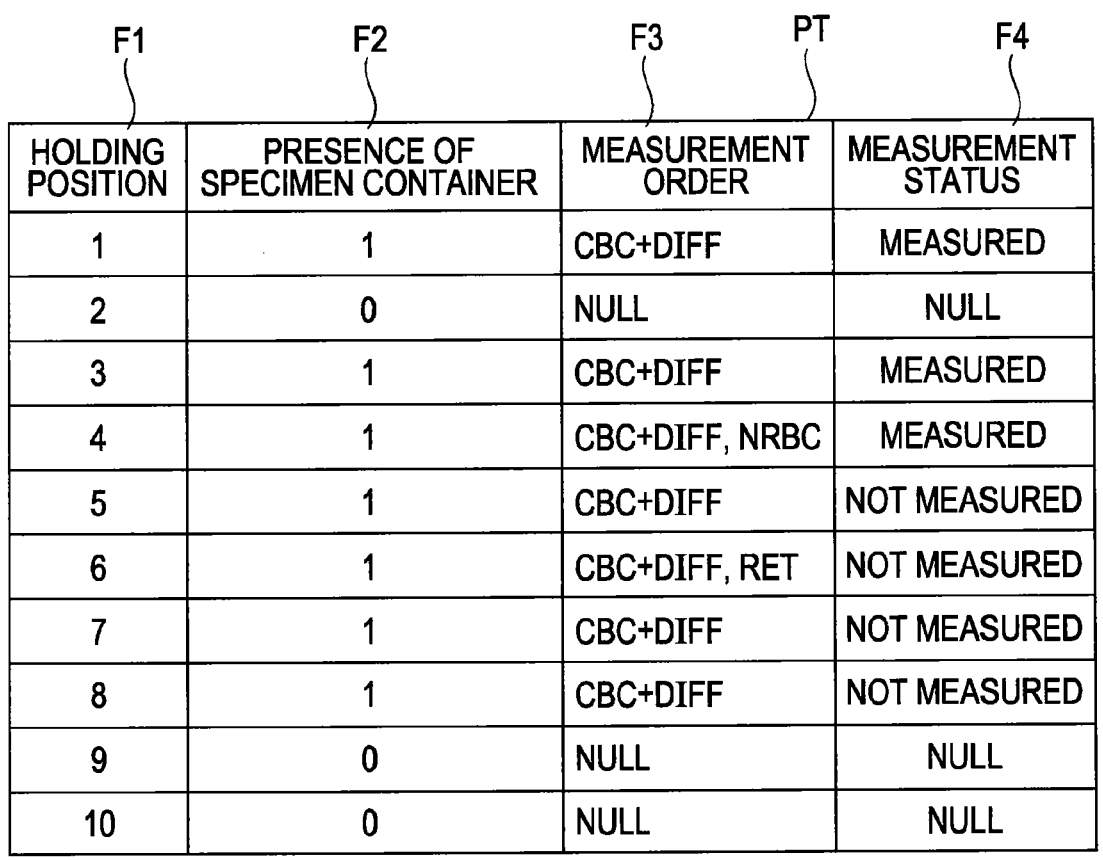
FIG. 11 is a schematic view showing a structure of a specimen processing table.

FIGS. 10A and 10B are flowcharts showing a flow of the specimen conveyance control process by the information processing unit 5 of the specimen processing device 1. The operator places the sample racks L holding the specimen containers T accommodating the specimen on the pre-analysis rack holder 41. In this state, the operator operates the input unit 53 and instructs the execution of the automatic calibration operation to the information processing unit 5. After accepting the instruction to execute the measurement of the specimen, the CPU 51a of the information processing unit 5 execute the following specimen conveyance control process. The CPU 51a first detects the sample rack L mounted on the pre-analysis rack holder 41 by a sensor (not shown) (step S101), and ensures a region of the specimen processing table used in the measurement of the specimen in the RAM 51c (step S102). FIG. 11 is a schematic view showing a structure of the specimen processing table. The specimen processing table PT is a table holding each information of the holding position in the sample rack L of each specimen, the presence of the specimen container, the measurement order, and the measurement status of the specimen for every sample rack L. As shown in FIG. 11, the specimen processing table PT includes ten rows, where each row corresponds to the specimen accommodated in the sample rack L. The specimen processing table PT includes a field (column) F1 of the holding position in the sample rack L, a field F2 of the presence of the specimen, a field F3 of the measurement order, and a field F4 of the measurement status. The field F1 stores information "1" to "10" indicating the holding position in the sample rack L of the specimen. The field F2 stores "1" if the specimen container T exists at the corresponding holding position, and stores "0" if the specimen container T does not exist at the corresponding holding position. The field F3 stores information of the measurement item indicated in the measurement order. As described above, the CBC+DIFF item includes each measurement item of WBC, RBC, PLT, HGB, NEUT, LYMPH, EO, BASO, and MONO, and thus the information of such measurement items may be stored individually in the field F3, or the information indicating "CBC+DIFF" may be stored in the field F3, as shown in FIG. 11. The field F4 stores one of the four types of information "not measured", "during specimen retrieval (first measurement unit)", "during specimen retrieval (second measurement unit", and "measured" as information indicating the measurement status. In step S102, each cell excluding the field F1 of the specimen processing table PT are all blank (stored with NULL) state. If two specimen processing tables PT exist, the following processes are performed with one specimen processing table PT as the target until all specimens of the sample rack L corresponding to the relevant one specimen processing table PT are processed and conveyed to the post-analysis rack holder 42, and thereafter, the following processes are performed with the other specimen processing table PT as the target.

The CPU 51a then references the state queues Q1, Q2 and stores the data indicating the states of the first measurement unit 2 and the second measurement unit 3 at a certain time point in the measurement unit state data regions S1, S2 (step S103). A plurality of state data is sometimes stored in the state queues Q1, Q2. In such a case, the CPU 51a sequentially retrieves the state data from the state queues Q1, Q2, and stores the data retrieved the last in the measurement unit state data regions S1, S2. The data retrieved the last from the state queues Q1, Q2 indicates the most recent state of the first measurement unit 2 and the second measurement unit 3, that is, indicates the state of the first measurement unit 2 and the second measurement unit 3 at the relevant time point. The initial value of the stats queue Q1, Q2 is "specimen retrievable".

The CPU 51a determines whether or not the sample rack L can be discharged (step S104). In this process, the CPU 51a references the specimen processing table PT, and if either one of "0" or "1" is stored in the field F2 for all holding positions (i.e., "NULL" cell does not exist) and "measured" is stored in the field F4 for all records stored with "1" in the field F2, the specimen container T held in the sample rack L does not need to be performed with the process and thus the sample rack L can be discharged. If "NULL" is stored in the field F2, or "not measured" or "during specimen retrieval" is stored in the field F4 with respect to at least one holding position, the specimen container T that needs to be performed with the process still remains in the sample rack L, and thus the sample rack L cannot be discharged.

If the sample rack L cannot be discharged in step S104 (NO in step S104), the CPU 51a determines whether or not a process-requiring specimen exists with reference to the specimen processing table PT (step S105). The "process-requiring specimen" refers to the specimen which measurement order is already confirmed and which is not measured. That is, in the specimen processing table PT, the information of the measurement order is stored in the field F3 and the specimen in which the information of "not measured" is stored in the field F4 is the "process-requiring specimen".

Figure 12:
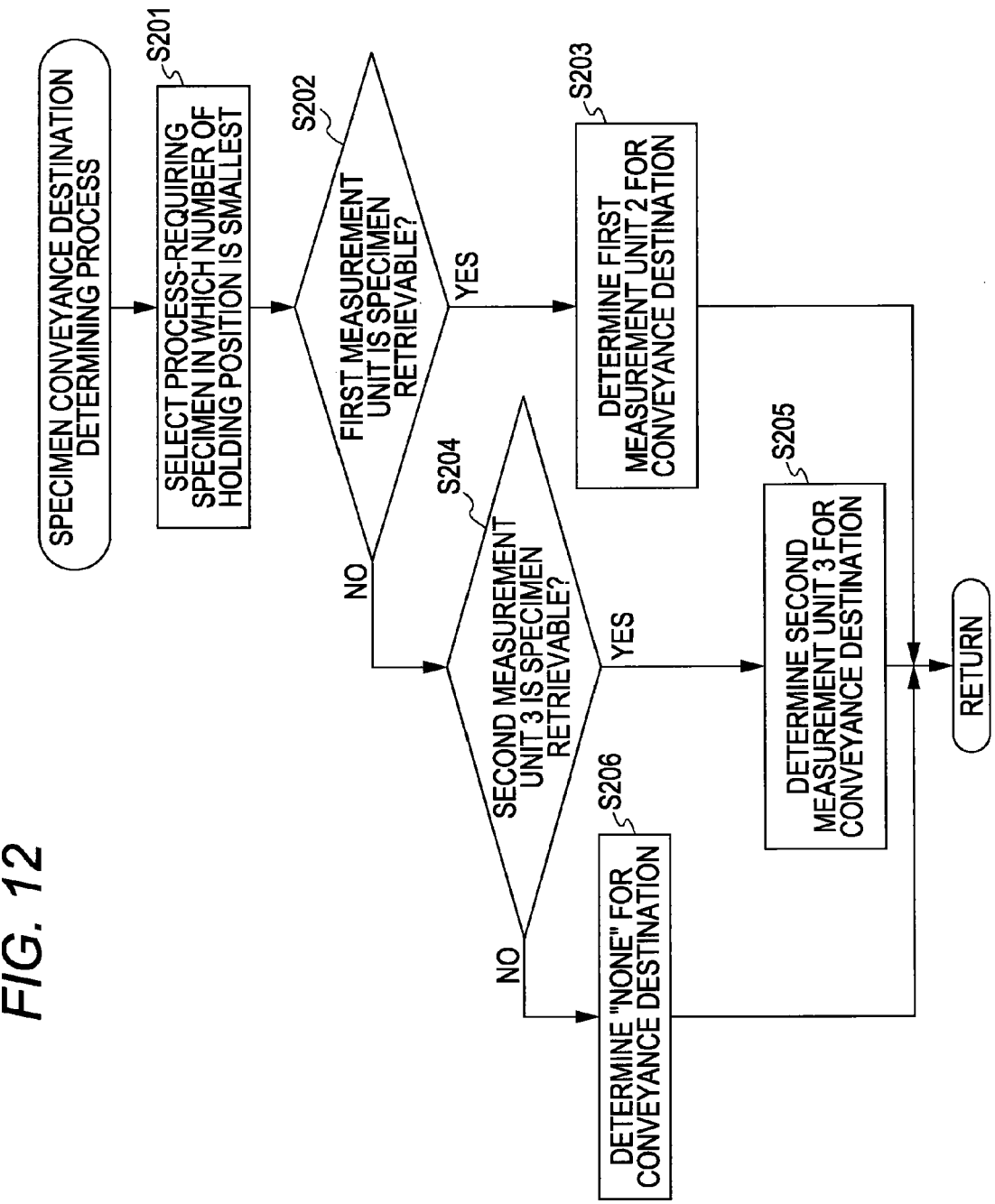
FIG. 12 is a flowchart showing the processing procedure of the specimen conveyance destination determining process by the CPU of the information processing unit of the specimen processing device.

If the process-requiring specimen exists in step S105 (YES in step S105), the CPU 51a executes the specimen conveyance destination determining process (step S106). FIG. 12 is a flowchart showing the procedures of the specimen conveyance destination determining process. In the specimen conveyance destination determining process, the CPU 51*a* first references the specimen processing table PT, and selects the process-requiring specimen in which the number of holding position is the smallest (step S201). The CPU 51*a* then references the measurement unit state data region S1 of the RAM 51*c*, and determines whether or not the state of the first measurement unit 2 is "specimen retrievable" (step S202). If the state of the first measurement unit 2 is "specimen retrievable" in step S202 (YES in step S202), the CPU 51*a* determines the first measurement unit 2 as the conveyance destination (step S203), and returns the process to the callout address of the specimen conveyance destination determining process.

If the state of the first measurement unit 2 is "specimen unretrievable/unreturnable" or "specimen returnable" (NO in step S202), the CPU 51*a* references the measurement unit state data region S2 of the RAM 51*c* and determines whether or not the state of the second measurement unit 3 is "specimen retrievable" (step S204). If the state of the second measurement unit 3 is "specimen retrievable" in step S204 (YES in step S204), the CPU 51*a* determines the second measurement unit 3 as the conveyance destination (step S205), and returns the process to the callout address of the specimen conveyance destination determining process.

If the state of the second measurement unit 3 is "unretrievable/unreturnable" or "specimen returnable" in step S204 (NO in step S204), the CPU 51*a* determines "none" for the conveyance destination (step S206), and returns the process to the callout address of the specimen conveyance destination determining process.

After the specimen conveyance destination determining process described above, the CPU 51*a* determines whether or not the determined conveyance destination is the first measurement unit 2 or the second measurement unit 3 (step S107), and conveys the specimen selected in the specimen conveyance destination determining process to the conveyance destination (step S108) if the determined conveyance destination is the first measurement unit 2 or the second measurement unit 3 (YES in step S107). In this process, the CPU 51*a* controls the specimen conveyance unit 4 so that the selected specimen is positioned at the first specimen supply position 43*a* when the conveyance destination is the first measurement unit 2, and controls the specimen conveyance unit 4 so that the selected specimen is positioned at the second specimen supply position 43*b* when the conveyance destination is the second measurement unit 3.

The CPU 51*a* inputs "specimen unretrievable/unreturnable" to the state queue corresponding to the measurement unit of the conveyance destination (step S109). The CPU 51*a* updates the specimen processing table PT by changing the measurement status in the specimen processing table PT of the specimen to "during specimen retrieval (first measurement unit)" to exclude the relevant specimen from the process-requiring specimen (step S110).

The CPU 51*a* also controls the specimen container conveyance unit of the measurement unit of the conveyance destination, and takes out the specimen container T at the specimen supply position from the sample rack L (step S111). Thereafter, the CPU 51*a* executes the specimen retrieval process and the specimen measurement process. The selected specimen container T is thereby retrieved inside the first measurement unit 2 or the second measurement unit 3, and the specimen is aspirated from the specimen container T. As the specimen retrieval process requires a few dozen seconds, the CPU 51*a* returns the process to step S103 after process of step S111 is terminated, and executes the processes of after step S103 in parallel with the specimen retrieval process.

If the process-requiring specimen does not exist in step S105 (NO in step S105), or if the conveyance destination determined by the specimen conveyance destination determining process in step S107 is "none" (NO in step S107), the CPU 51*a* references the measurement unit state data regions S1, S2 and determines whether or not the measurement unit in which the device state is "specimen returnable" exists (step S112). If at least either one of the state information stored in the measurement unit state data region S1, S2 is "specimen returnable" (YES in step S112), the CPU 51*a* conveys the sample rack L to one of the first measurement unit 2 or the second measurement unit 3 in the state of "specimen returnable" (step S113). In this process, if the "specimen returnable" is stored in the measurement unit state data region S1, the CPU 51*a* references the specimen processing table PT and conveys the sample rack L so that the holding position corresponding to the record in which "during specimen retrieval (first measurement unit)" is stored in the field F4 is positioned at the first specimen supply position 43*a*. If the "specimen returnable" is stored in the measurement unit state data region S2, the CPU 51*a* references the specimen processing table PT and conveys the sample rack L so that the holding position corresponding to the record in which "during specimen retrieval (second measurement unit)" is stored in the field F4 is positioned at the second specimen supply position 43*b*. If both the first measurement unit 2 and the second measurement unit 3 are in the state of "specimen returnable", the CPU 51*a* conveys the sample rack L with the first measurement unit 2 as the conveyance destination.

The CPU 51*a* then executes the specimen return process (step S114). In the specimen return process, one of the first measurement unit 2 or the second measurement unit 3 in the state of "specimen returnable" is controlled, and the retrieved specimen container T is discharged from the measurement unit and returned to the sample rack L. In the specimen return process, the specimen processing table PT is updated by changing the measurement status in the specimen processing table PT of the returned specimen to "measured". The details on the specimen return process will be described later. The CPU 51*a* returns the process to step S103 after the specimen return process is terminated.

If "specimen returnable" is not stored in both measurement unit state data regions S1, S2 in step S112 (NO in step S112), the CPU 51*a* references the specimen processing table PT and determines whether or not the holding position at where the measurement unit is unconfirmed, that is, the holding position where the information "0" indicating no specimen is not stored at the field F2 in the specimen processing table PT and the information of the measurement order is not stored in the field F3 exists (step S115).

If the holding position where the measurement order is unconfirmed exists in step S115 (YES in step S115), the CPU 51*a* controls the specimen conveyance unit 4 to convey the sample rack L, and positions one of the holding positions where the measurement order is unconfirmed of the holding positions of the sample rack L at the reading position 43*d* on the front side of the barcode reading unit 44 (step S116). The holding position to be positioned at the reading position 43*d* is the holding position having the smallest number (holding position on the most downstream side in the conveyance direction of the sample rack L) of the holding positions where "0" is not stored in the field F2 in the specimen processing table PT and the information of the measurement order is not stored in the field F3. That is, if the specimen in which the measurement order is confirmed does not exist at all, the holding position "1" is selected, and the sample rack L is conveyed such that the holding position "1" is positioned at the reading position 43d. If the measurement orders of all specimens other than the specimen in which the holding position is "1" are unconfirmed, the holding position "2" is selected, and the sample rack L is conveyed such that the holding position "2" is positioned at the reading position 43d. Thus, the holding positions are positioned at the reading position 43d in order from small numbers.

After conveying the sample rack L such that the selected holding position is positioned at the reading position 43d, the CPU 51a determines whether or not the specimen container T is detected by the specimen container sensor 45 (step S117). If the specimen container T is detected (YES in step S117), the specimen ID is read by the barcode reading unit 44 from the specimen barcode of the specimen container T (step S118).

The CPU 51a then executes the measurement order acquiring process, as described later. The CPU 51a acquires the measurement order of the relevant specimen by such a process. The measurement order acquiring process is executed in parallel with the specimen conveyance control process by the multitask process. The sample rack L thus can be conveyed while executing the measurement order acquiring process.

If the specimen container T is not detected in step S117 (NO in step S117), the CPU 51a stores "0" to the cell corresponding to the relevant holding position of the field F2 of the specimen processing table PT (step S119), and returns the process to step S115.

If the holding position where the measurement is unconfirmed does not exist in step S115 (NO in step S115), the CPU 51a determines whether or not a new sample rack L can be sent to the conveyance unit 43 (step S120). In step S120, the CPU 51a assumes that a new sample rack L can be conveyed if the sample rack L mounted on the pre-analysis rack holder 41 is detected by the sensor (not shown), and either "0" or "1" is stored in the field F2 (i.e., cell of "NULL" does not exist) for all holding positions before a predetermined holding position (e.g., holding position "7") in the specimen processing table PT related to the sample rack L currently being conveyed by the conveyance unit 43, and "measured" is stored in the field F4 for all records in which "1" is stored in the field F2. That is, a new sample rack L can be conveyed if a new sample rack L is mounted on the pre-analysis rack holder 41, and retrieval and return of the specimen are completed for the specimen of each holding position before the predetermined holding position of the sample rack L currently being conveyed. Therefore, if "NULL" is stored in the field F2, or "not measured" or "during specimen retrieval" is stored in the field F4 for even one holding position before the predetermined holding position, a new sample rack L cannot be conveyed.

If a new sample L can be conveyed in step S120 (YES in step S120), the CPU 51a newly ensures the region of the specimen processing table in the RAM 51c (step S121). Furthermore, the CPU 51a controls the rack sending portion 41b to transfer the new sample rack L to the pre-analysis rack holder 41 and send the same to the rack conveyance unit 43 (step S122). In this case, the conveyance control of the conveyance unit 43 is performed so that the sample rack L currently being conveyed and the newly sent sample rack L do not interfere, and then the new sample rack L is sent to the rack conveyance unit 43. After the process of step S122 is terminated, the CPU 51a returns the process to step S103.

If a new sample rack L cannot be conveyed in step S120 (NO in step S120), the CPU 51a waits for a predetermined time (e.g., for one second) (step S123), returns the process to step S103, and references the state queues Q1 and Q2 and stores the data indicating the states of the first measurement unit 2 and the second measurement unit 3 at a relevant time point in the measurement unit state data regions S1, S2 (step S103).

If the measurement status of all specimens is "measured" in the specimen processing table PT in step S104 (YES in step S104), the CPU 51a controls the specimen conveyance unit 4 (step S124) so as to convey the sample rack L (sample rack L on left side if two sample racks L exist on the rack conveyance unit 43) to the post-analysis rack holder 42 by the rack conveyance unit 43, releases the region of the specimen processing table PT corresponding to the relevant sample rack L in the RAM 51c (step S125), and returns the process to step S103.

<Measurement Order Acquiring Process>

Figure 13:
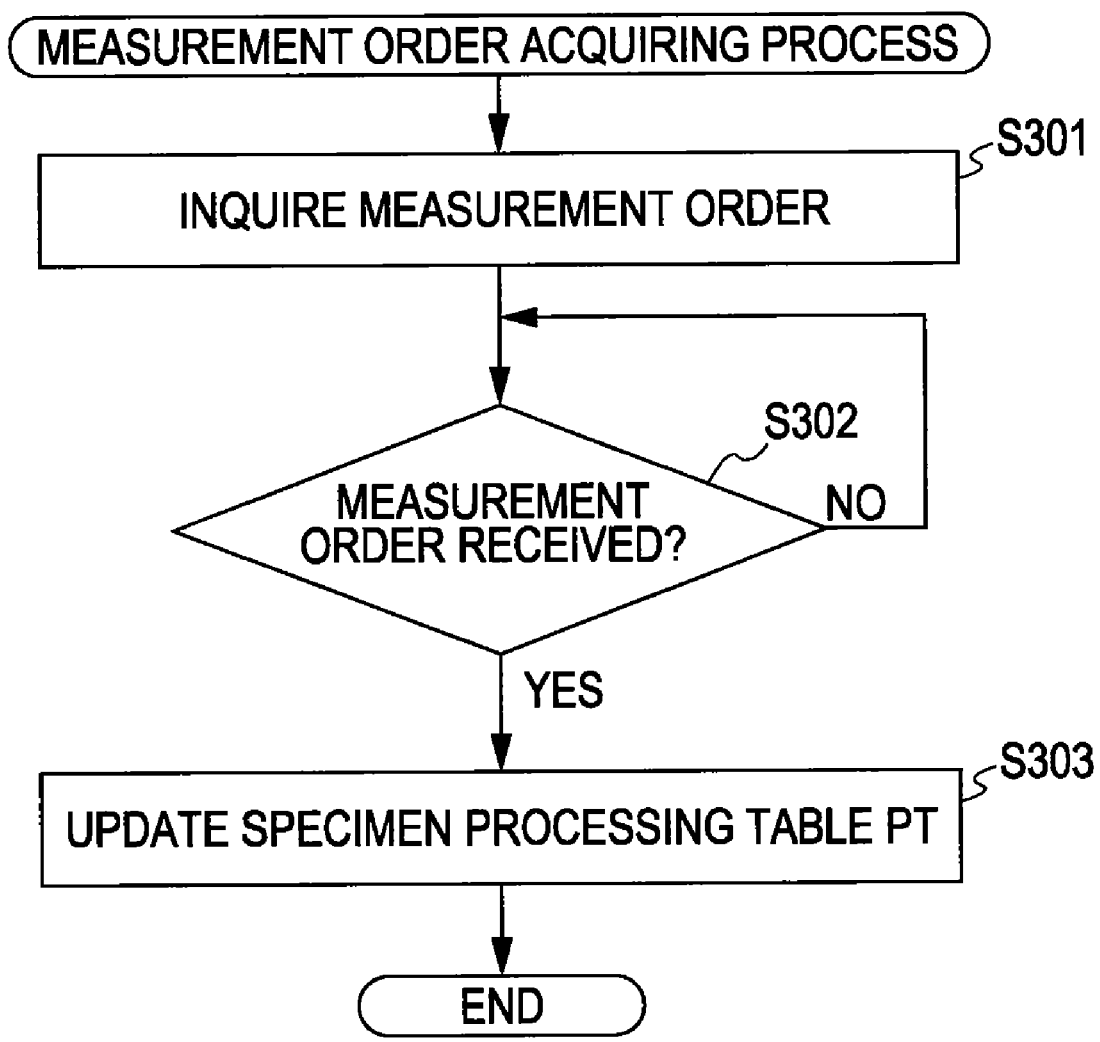
FIG. 13 is a flowchart showing a flow of the measurement order acquiring process by the CPU of the information processing unit of the specimen processing device.

The measurement order acquiring process by the information processing unit 5 will now be described. FIG. 13 is a flowchart showing a flow of the measurement order acquiring process by the information processing unit 5 of the specimen processing device 1.

In the measurement order acquiring process, the CPU 51a first inquires the host computer 6 on the measurement order corresponding to the relevant specimen ID (step S301). This is performed by transmitting the measurement order request data including the specimen ID to the host computer 6 connected through the network. The CPU 51a waits for the reception of the measurement order (NO in step S302), and when receiving the measurement order (YES in step S302), updates the specimen processing table PT (step S303) by storing "1" to the cell of the field F2 of the presence of the specimen container corresponding to the holding position, storing the measurement order to the cell of the field F3 of the measurement order, and storing the information "not measured" in the field of the measurement status in the specimen processing table PT, and terminates the measurement order acquiring process.

The measurement order acquiring process described above is executed in parallel with the specimen conveyance control process by the multi-task process. Thus, the sample rack L can be conveyed while executing the measurement order acquiring process.

<Specimen Retrieval Process>

Figure 14:
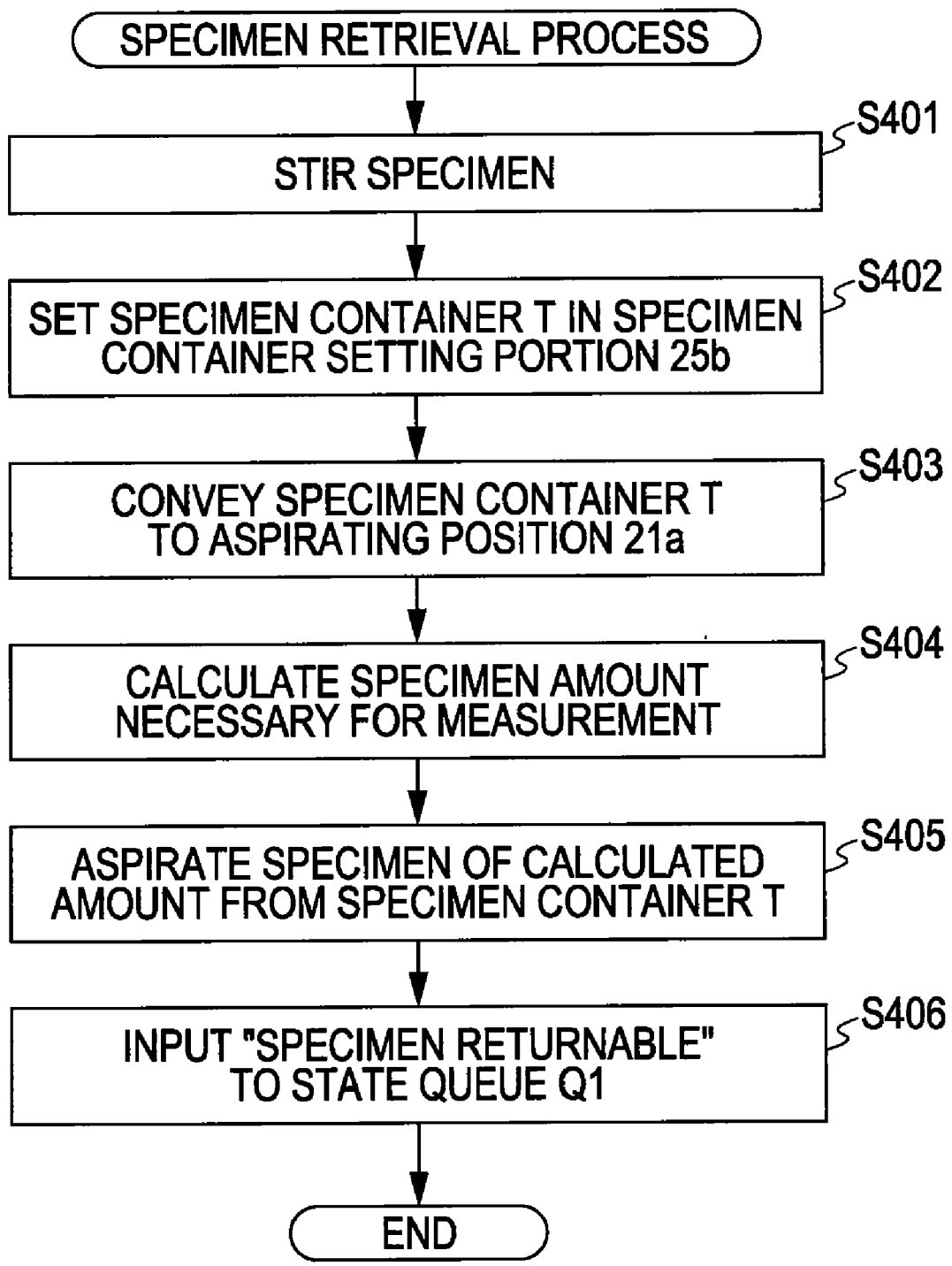
FIG. 14 is a flowchart showing a flow of the specimen retrievable process by the CPU of the information processing unit of the specimen processing device.

The measurement order acquiring process by the information processing unit 5 will now be described. FIG. 14 is a flowchart showing a flow of the specimen retrieval process by the information processing unit 5 of the specimen processing device 1. The specimen retrieval process by the first measurement unit 2 will be described here, but the specimen retrieval process by the second measurement unit 3 is a similar process.

As described above, the specimen retrieval process by the first measurement unit 2 is executed by the CPU 51a after taking out the specimen container T at the first specimen supply position 43a from the sample rack L. In the specimen retrieval process by the first measurement unit 2, the CPU 51a first controls the hand portion 25a to oscillate the specimen container T, and stirs the specimen in side for a predetermined time (step S401). About a few dozen seconds is required to stir the specimen. The CPU 51a then controls the hand portion 25a and sets the specimen container T at the specimen container setting portion 25b (step S402), and also controls the specimen container conveyance portion 25 to convey the specimen container T to the aspirating position (step S403). The CPU 51a also references the measurement order of the retrieved specimen, and calculates the specimen amount necessary for the measurement from the measurement item (step S404). The CPU 51a controls the specimen aspirating portion 21 to aspirate the specimen of an amount necessary for the measurement from the specimen container T (step S405). After the process of step S405 is terminated, the CPU 51a inputs the information "specimen returnable" to the state queue Q1 (step S406) since the first measurement unit 2 is in the specimen returnable state, and terminates the process.

The specimen retrieval process described above is executed in parallel with the specimen conveyance control process by the multi-task process. Thus, the sample rack L can be conveyed while executing the specimen retrieval process.

<Specimen Retrieval Process>

Figure 15:
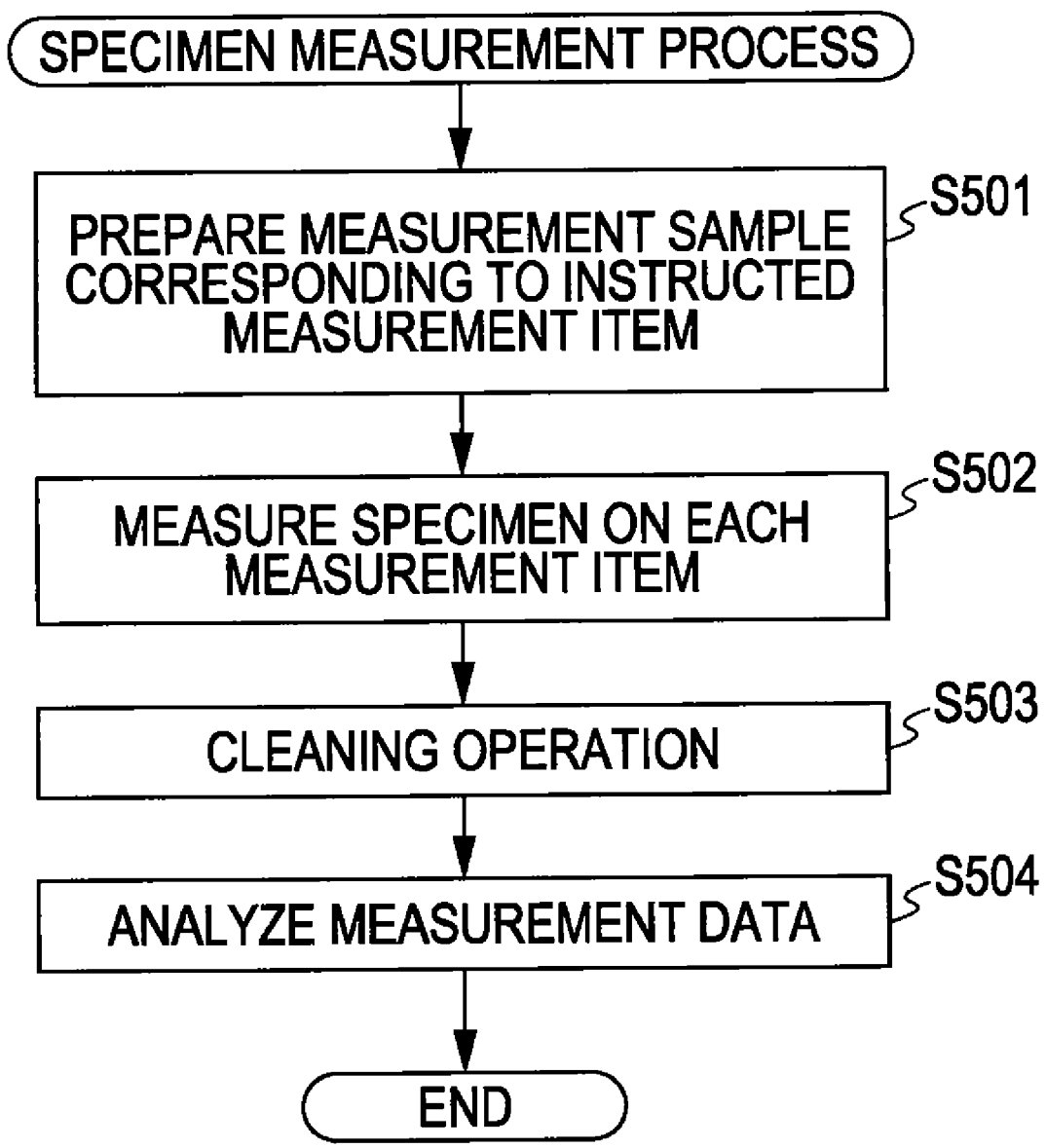
FIG. 15 is a flowchart showing a flow of the specimen measurement process by the CPU of the information processing unit of the specimen processing device.

The measurement order acquiring process by the information processing unit 5 will now be described. FIG. 15 is a flowchart showing a flow of the specimen measurement process by the information processing unit 5 of the specimen processing device 1. The specimen measurement process by the first measurement unit 2 will be described here, but the specimen measurement process by the second measurement unit 3 is a similar process.

After the specimen retrieval process is terminated, the CPU 51a executes the specimen measurement process. In the specimen measurement process, the CPU 51a first controls a sample preparing unit 22 to prepare the measurement sample corresponding to the measurement item (step S501). The CPU 51a then supplies the measurement sample to the detection unit 23 to measure the specimen on each measurement item contained in the measurement order by the detection unit 23 (step S502). The CPU 51a thereby acquires the measurement data output from the detecting portion 23. The CPU 51a then executes a cleaning operation of cleaning a flow path, a reaction chamber, and the like used in the measurement (step S503).

The CPU 51a executes the analyzing process of the measurement data (step S504), and obtains the analysis result including the numerical values and the like of RBC, PLT, HGB, WBC, NEUT, LYMPH, EO, BASO, and MONO. After the process of step S504 is completed, the CPU 51a terminates the process.

The specimen measurement process described above is executed in parallel with the specimen conveyance control process by the multi-task process. Thus, the sample rack L can be conveyed while executing the specimen measurement process.

<Specimen Return Process>

Figure 16:
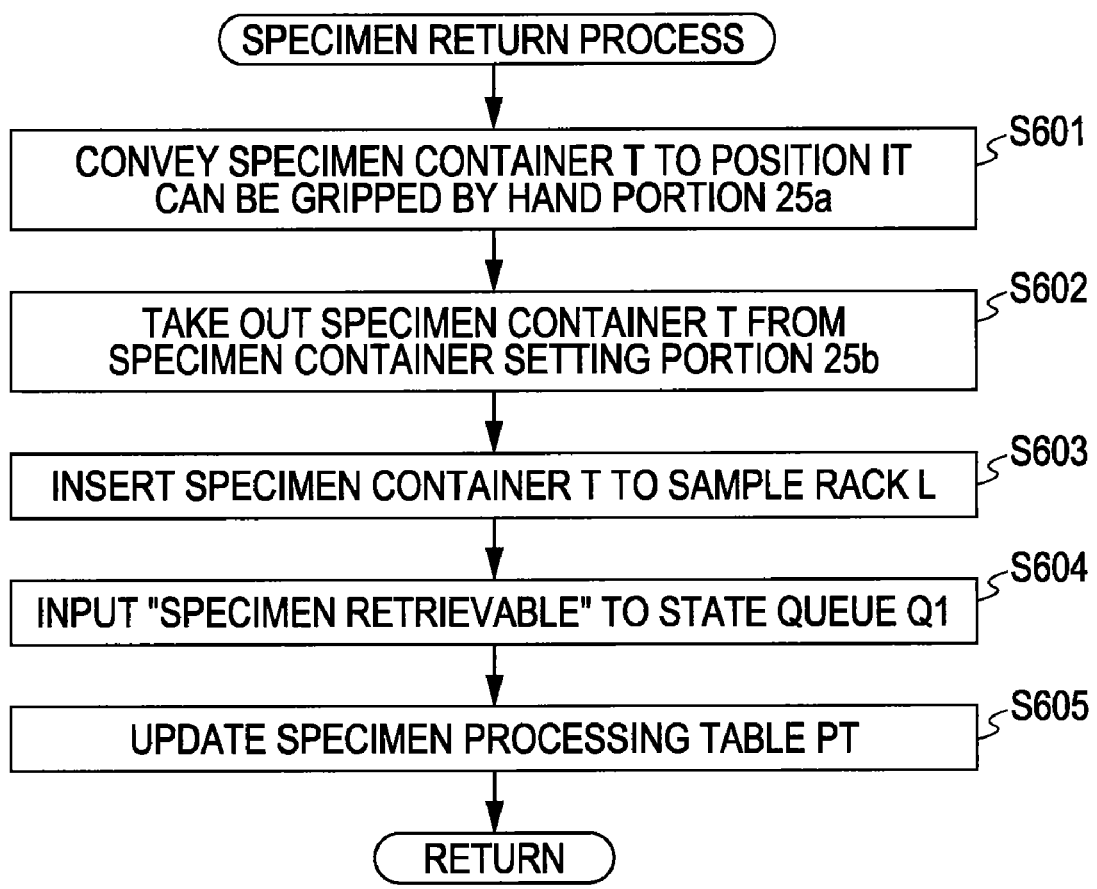
FIG. 16 is a flowchart showing a procedure of the specimen return process by the CPU of the information processing unit of the specimen processing device of the specimen processing device.

The measurement order acquiring process by the information processing unit 5 will now be described. FIG. 16 is a flowchart showing a flow of the specimen return process by the information processing unit 5 of the specimen processing device 1. The specimen return process by the first measurement unit 2 will be described here, but the specimen return process by the second measurement unit 3 is a similar process.

In the specimen return process, the CPU 51a first controls the specimen container conveyance unit 25, moves the specimen container setting portion 25b from the aspirating position, and conveys the specimen container T to the position where it can be gripped by the hand portion 25a (step S601). The CPU 51a then controls the hand portion 25a to grip the specimen container T with the hand portion 25a, and takes out the specimen container T from the specimen container setting portion 25a (step S602). The CPU 51a also controls the hand portion 25a and inserts the gripped specimen container T to the holding position of the sample rack L of the first specimen supply position 43a (step S603).

Since the first measurement unit 2 is in the specimen retrieval state, the CPU 51a inputs "specimen retrievable" to the state queue Q1 of the RAM 51c (step S604). The CPU 51a updates the measurement status in the specimen processing table PT of the specimen returned to the sample rack L to "measured" (step S605). After the process of step S605 is completed, the CPU 51a returns the process to the call out address of the first specimen analyzing process.

The operation of the specimen processing device 1 will now be described using specific examples. The operation of the specimen processing device 1 when the sample rack L holding the specimen in which the CBC+DIFF is included in the measurement item at each holding position 1 to 10 is inserted to the specimen processing device 1 will be de described.

Figure 17:
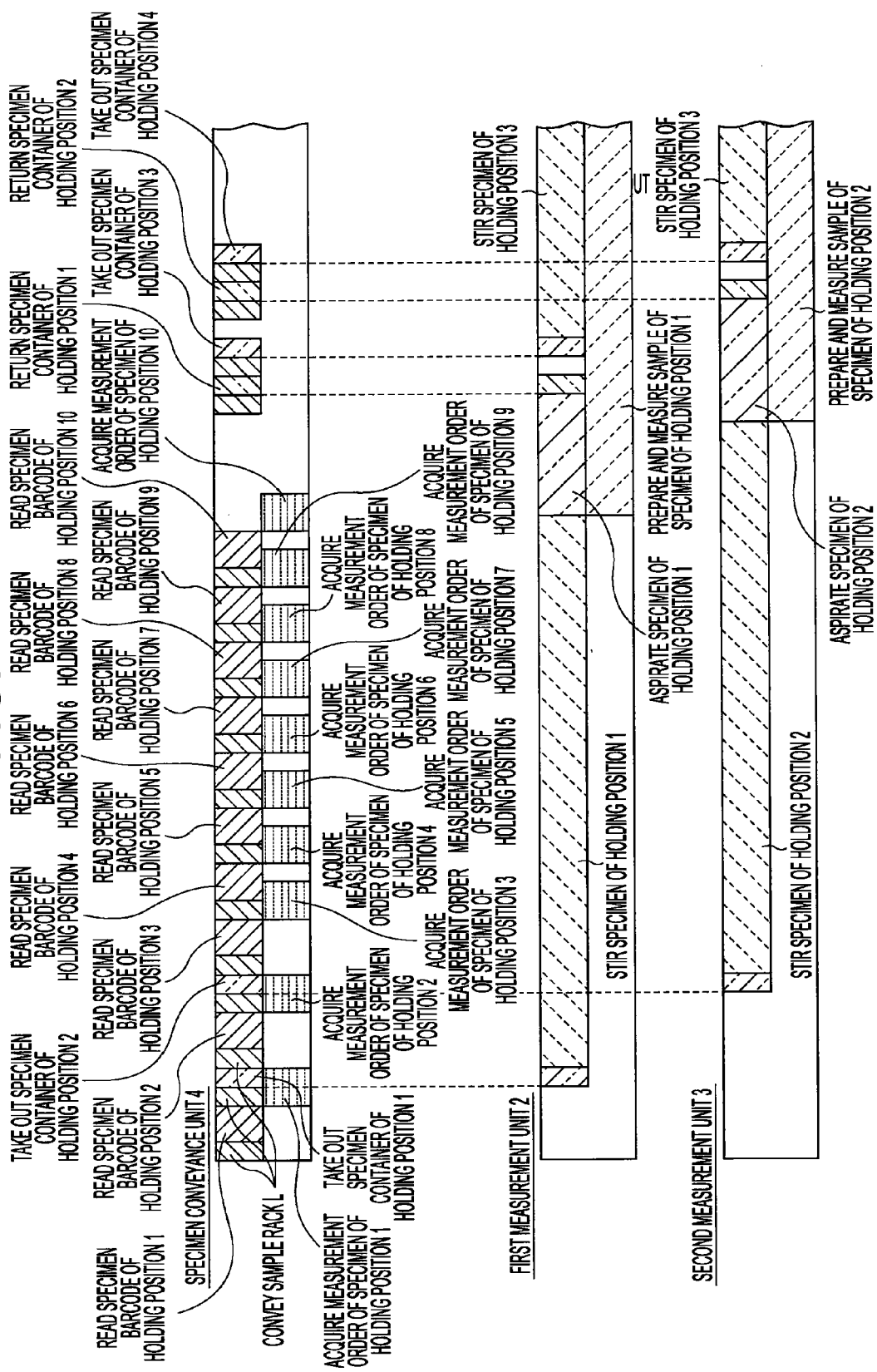
FIG. 17 is a timing chart showing the operation of the first measurement unit and the second measurement unit of the specimen processing device when the sample rack is inserted to the specimen processing device.
Figure 18C:
FIG. 18C is a view schematically showing one example of a state of the specimen processing table.

FIG. 17 is a timing chart showing the operation of the first measurement unit 2 and the second measurement unit 3 of the specimen processing device 1 when the sample rack L is inserted to the specimen processing device 1. First, when the sample rack L is inserted to the pre-analysis rack holder 41 and the execution of the specimen measurement is instructed from the operator to the information processing unit 5, the sample rack L mounted on the pre-analysis rack holder 41 is detected (step S101 in FIG. 10A), and the region of the specimen processing table PT is ensured in the information processing unit 5 (step S102). FIGS. 18A to 18G are views schematically showing a state of the specimen processing table PT. The state of the specimen processing table PT at the relevant time point is shown in FIG. 18A. At this time point, the specimen processing table PT is in a state the data of NULL is stored in all the cells other than the field F1.

The state queues Q1, Q2 are then referenced by the CPU 51a, and the data input last to each state queue Q1, Q2 is stored in the measurement unit state data region S1, S2 (step S103). Since only the initial value "specimen retrieval" is input to the state queues Q1, Q2, "specimen retrievable" is stored in each measurement unit state data regions S1, S2.

Whether or not the sample rack L can be discharged is then determined by the CPU 51a (step S104), but the process of the CPU 51a proceeds to step S105 since "NULL" is stored in all fields F2 of the presence of the specimen container of the specimen processing table PT (NO in step S104). Whether or not the process-requiring specimen exists is determined in step S105, but the process of the CPU 51a proceeds to step S112 since not even one process-requiring specimen exists in the specimen processing table PT (NO in step S105).

Whether or not the measurement unit in which the device state is "specimen returnable" exists is determined by the CPU 51a (step S112). The process of the CPU 51a proceeds to step S115 since "specimen returnable" is stored in both measurement unit state data regions S1, S2 (NO in step S112").

Whether or not the holding position at which the measurement order is unconfirmed exists is determined by the CPU 51a (step S115). Not even one record in which the information of the measurement order is stored in the field F3 of the measurement order exists in the specimen processing table PT. That is, only the specimen in which the measurement order is unconfirmed exists (YES in step S115). The CPU 51a thus proceeds the process to step S116.

Among the specimens accommodated in the specimen rack L, one of the holding positions in which the measurement order is unconfirmed is conveyed up to the reading position 43d on the front side of the barcode reading unit 44 (step S116). Since the specimen in which the measurement order is confirmed does not exist at all, the sample rack L is conveyed until the holding position 1 is positioned at the reading position 43d. The specimen container T is detected by the specimen container sensor 45 (YES in step S117) since the specimen container T is held at the holding position 1 of the sample rack L. Therefore, the specimen ID is read by the barcode reading unit 44 from the barcode of the specimen at the holding position 1 (step S118), and the measurement order acquiring process is executed.

In the measurement order acquiring process, the measurement order of the specimen at the holding position 1, that is, the measurement order including the CBC+DIFF item is acquired from the host computer 6 by the CPU 51a (steps S301, S302). The specimen processing table PT is then updated (step S303). The state of the specimen processing table PT in this case is shown in FIG. 18B. As shown in the figure, "1" is stored in the field F2 of the presence of the specimen container T in the row of the holding position 1 of the specimen processing table PT, the information indicating "CBC+DIFF" is stored in the field F3 of the measurement order, and the information indicating "not measured" is stored in the field F4 of the measurement status.

As shown in FIG. 17, the specimen conveyance control process is continuously executed in parallel to the measurement order acquiring process. That is, the process of step S103 is again executed by the CPU 51a, and the state queues Q1, Q2 are referenced by the CPU 51a and the data input last to each state queue Q1, Q2 is stored in the measurement unit state data region S1, S2 (step S103). The data of the measurement unit state data regions S1, S2 are not changed since data does not exist in the state queues Q1, Q2. That is, "specimen retrievable" is stored in each measurement unit state data region 51, S2.

The process of step S104 is then executed and whether or not the sample rack L is dischargeable is determined, but since the sample rack L is not dischargeable (NO in step S104), whether or not the process-requiring specimen exists is determined in step S105. The specimen of the holding position 1 is the process-requiring specimen since the information of the measurement order exists in the specimen processing table PT and the measurement status is "not measured". Therefore, the specimen conveyance destination determining process S106 is executed by the CPU 51a.

In the specimen conveyance destination determining process, the process-requiring specimen in which the number of the holding position is the smallest in the specimen processing table PT is selected by the CPU 51a (step S201). The specimen of the holding position 1 is then selected, and whether or not the first measurement unit 2 is in the specimen retrievable state is determined by the measurement unit state data region S1 of the RAM 51c (step S202). The information of "specimen retrievable" is held in both the measurement unit state data regions S1, S2. Therefore, the first measurement unit 2 is determined as specimen retrievable (YES in step S202), the first measurement unit 2 is determined as the conveyance destination (step S203), and the process is returned to the callout address of the specimen conveyance destination determining process S106.

Whether or not the determined conveyance destination is the first measurement unit 2 or the second measurement unit 3 is determined by the CPU 51a (step S107), where the conveyance destination is determined as the first measurement unit 2 (YES in step S107), and thus the specimen of the holding position 1 is conveyed to the first specimen supply position 43a (step S108).

That is, if the specimen barcode reading is performed on the specimen container T of the holding position 1, and both the first measurement unit 2 and the second measurement unit 3 are not executing the specimen measurement, the first measurement unit 2 is preferentially selected over the second measurement unit 3 as the specimen supply destination, and the specimen container T is conveyed to the first specimen supply position 43a to supply the specimen container T of the holding position 1 to the first measurement unit 2.

This will be described with reference to FIG. 9. The sample rack L is conveyed until the holding position 1 is positioned at the reading position 43d, and the specimen ID is read by the barcode reading unit 44 from the barcode of the specimen container T at the holding position 1 of the sample rack L (step S001). At this time point, the first measurement unit 2 is not performing specimen process (NO in step S002), and the second measurement unit 3 is not performing the specimen process (NO in step S004), and thus the specimen container T of the holding position 1 is conveyed to the first specimen supply position 43a (step S005).

Returning back to FIG. 10A, "specimen unretrievable/unreturnable" is input to the state queue Q1 of the RAM 51c by the CPU 51a (step S109), and the measurement status of the holding position 1 of the specimen processing table PT is changed to "during specimen retrievable (first measurement unit)" (step S110). The specimen container T of the holding position 1 at the first specimen supply position 43a is taken out from the sample rack L (step S111). The state of the specimen processing table PT in this case is shown in FIG. 18C. Thereafter, the specimen retrieval process by the first measurement unit 2 is executed, and the specimen container T is retrieved inside the first measurement unit 2 (steps S401 to 405).

The sample rack L can be conveyed even if the specimen container T of the holding position 1 is taken out. The CPU 51a again executes the processes after step S103 during a few dozen seconds in which the specimen container T is retrieved into the first measurement unit 2. At this point, the data input last to the state queue Q1 is "specimen unretrievable/unreturnable", and thus the information "specimen unretrievable/unreturnable" is stored in the measurement unit state data region S1 (step S103). As shown in FIG. 18C, the sample rack L is not dischargeable since "NULL" is stored in the field F2 of the holding positions 2 to 10 (NO in step S104), the process-requiring specimen does not exist (NO in step S105), and the measurement unit in which the device state is "specimen returnable" does not exist (NO in step S112). Since the holding position at where the measurement order is unconfirmed exists (YES in step S115), the holding position 2 of the smallest number of the holding positions where the measurement order is unconfirmed is positioned at the reading position 43d (step S116) and the specimen container T is held at the holding position 2, and thus the specimen container T is detected by the specimen container sensor 45 (YES in step S117). Therefore, the specimen ID is read by the barcode reading unit 44 from the barcode of the specimen of the holding position 2 (step S118), and the measurement order acquiring process is executed.

Figure 18D:
FIG. 18D is a view schematically showing one example of a state of the specimen processing table.

In the measurement order acquiring process, the measurement order of the specimen of the holding position 2, that is, the measurement order including the CBC+DIFF item is acquired from the host computer 6 by the CPU 51a (steps S301, S302). The specimen processing table PT is then updated (step S303). The state of the specimen processing table PT in this case is shown in FIG. 18D. As shown in the figure, "1" is stored in the field F2 of the presence of the specimen container T in the row of the holding position 2 of the specimen processing table PT, the information indicating "CBC+DIFF" is stored in the field F3 of the measurement order, and the information indicating "not measured" is stored in the field F4 of the measurement status.

As shown in FIG. 17, the specimen conveyance control process is continuously executed in parallel with the measurement order acquiring process. That is, the process of step S103 is again executed by the CPU 51*a*. Since the data does not exist in the state queues Q1, Q2 at this point, the data of the measurement unit state data regions S1, S2 is not changed in the process of step S103. That is, "specimen unretrievable/unreturnable" is stored in the measurement unit state data region S1, and "specimen retrievable" is stored in the measurement unit state data region S2.

As shown in FIG. 18D, the sample rack L is not dischargeable since "NULL" is stored in the field F2 of the holding positions 3 to 10 (NO in step S104), and whether or the process-requiring specimen exists is determined in step S105. The specimen of the holding position 2 is the process-requiring specimen since the information of the measurement order exists in the specimen processing table PT and the measurement status is "not measured". Therefore, the specimen conveyance destination determining process S106 is executed by the CPU 51*a*.

In the specimen conveyance destination determining process, the process-requiring specimen in which the number of the holding position is the smallest in the specimen processing table PT is selected by the CPU 51*a* (step S201). The specimen of the holding position 2 is then selected, and whether or not the first measurement unit 2 is in the specimen retrievable state is determined by the measurement unit state data region S1 of the RAM 51*c* (step S202). The information of "specimen unretrievable/unreturnable" is held in the measurement unit state data region S1. Therefore, the first measurement unit 2 is determined as specimen unretrievable (NO in step S202), and whether or not the second measurement unit 3 is in the specimen retrievable state is determined by the measurement unit state data region S2 of the RAM 51*c* (step S204). The information "specimen retrievable" is held in the measurement unit state data region S2. Therefore, the second measurement unit 3 is determined as specimen retrievable (YES in step S204), the second measurement unit 3 is determined as the conveyance destination (step S205), and the process is returned to the callout address of the specimen conveyance destination determining process S106.

The CPU 51*a* determines whether or not the determined conveyance destination is the first measurement unit 2 or the second measurement unit 3 (step S107), and conveys the specimen of the holding position 2 to the second specimen supply position 43*b* (step S108) since the conveyance destination is determined as the second measurement unit 3 (YES in step S107).

That is, when the specimen barcode reading is performed on the specimen container T of the holding position 2, the first measurement unit 2 executes the specimen measurement, and the second measurement unit 3 does not execute the specimen measurement, the second measurement unit 3 is selected as the specimen supply destination, and the specimen container T is conveyed to the second specimen supply position 43*b* to supply the relevant specimen container T of the holding position 2 to the second measurement unit 3.

This will be described with reference to FIG. 9. The sample rack L is conveyed until the holding position 2 is positioned at the reading position 43*d*, and the specimen ID is read by the barcode reading unit 44 from the barcode of the specimen container T of the holding position 2 of the sample rack L (step S001). At this time point, the first measurement unit 2 performs the processing of the specimen (YES in step S002) and the second measurement unit 3 does not perform the processing of the specimen (NO in step S003), and thus the specimen container T of the holding position 2 is conveyed to the second specimen supply position 43*b* (step S007).

Figure 18E:
FIG. 18E is a view schematically showing one example of a state of the specimen processing table.

Returning back to FIG. 10A, "specimen unretrievable/unreturnable" is input to the state queue Q2 of the RAM 51*c* by the CPU 51*a* (step S109), and the measurement status of the holding position 2 of the specimen processing table PT is changed to "during specimen retrievable (second measurement unit)" (step S110). The specimen container T of the holding position 2 at the second specimen supply position 43*b* is taken out from the sample rack L (step S111). The state of the specimen processing table PT in this case is shown in FIG. 18E. Thereafter, the specimen retrieval process by the second measurement unit 3 is executed, and the specimen container T is retrieved inside the second measurement unit 3 (steps S401 to 405). As shown in FIG. 17, the specimen retrieval process of the specimen container T of the holding position 1 is also executed in parallel.

A time of about a few dozen seconds is required until the retrieval of the specimen container T is completed. The CPU 51*a* continues the specimen conveyance control process while the specimen retrieval process is being executed for the specimen of the holding positions 1 and 2. The specimen measurement process is executed when the specimen retrieval is completed. The specimen measurement process is executed in parallel with the specimen conveyance control process.

The CPU 51*a* again executes the processes after step S103 while the specimen retrieval process by the first measurement unit 2 and the second measurement unit 3 is being executed. At this point, the data input last to the state queue Q2 is "specimen unretrievable/unreturnable", and thus the information "specimen unretrievable/unreturnable" is stored in the measurement unit state data region S2. Since the data is not input to the state queue Q1, the data stored in the measurement unit state data region S1 remains to be "specimen unretrievable/unreturnable" without being changed (step S103).

As shown in FIG. 18E, the sample rack L is not dischargeable since the information indicating the presence of the specimen container T of holding positions 3 to 10 in the specimen processing table PT is "NULL" (NO in step S104), the process-requiring specimen does not exist (NO in step S105), and the measurement order of the specimen of the holding positions 3 to 10 is unconfirmed (YES in step S115), and thus the holding position 3 having the smallest number of the holding positions in which the measurement order is unconfirmed is positioned at the reading position 43*d* (step S116), and the specimen container T is held at the holding position 3, whereby the specimen container T is detected by the specimen container sensor (YES in step S117). Therefore, the specimen ID is read by the barcode reading unit 44 from the barcode of the specimen of the holding position 3 (step S118), and the measurement order acquiring process is executed.

In the measurement order acquiring process, the measurement order of the specimen of the holding position 3, that is, the measurement order including the CBC+DIFF item is acquired from the host computer 6 by the CPU 51*a* (steps S301, S302). The specimen processing table PT is then updated (step S303). The state of the specimen processing table PT in this case is shown in FIG. 18F. As shown in the figure, "1" is stored in the field F2 of the presence of the specimen container T in the row of the holding position 3 of the specimen processing table PT, the information indicating "CBC+DIFF" is stored in the field F3 of the measurement order, and the information indicating "not measured" is stored in the field F4 of the measurement status.

As shown in FIG. 17, the specimen conveyance control process is continuously executed in parallel with the measurement order acquiring process. That is, the process of step S103 is again executed by the CPU 51*a*. Since the data does not exist in the state queues Q1, Q2 at this point, the data of the measurement unit state data regions S1, S2 is not changed in the process of step S103. That is, "specimen unretrievable/unreturnable" is stored in the measurement unit state data regions S1, S2.

As shown in FIG. 18F, the information of the presence of the specimen container T of the holding positions 4 to 10 is "NULL" (NO in step S104), and thus whether or the process-requiring specimen exists is determined in step S105. The specimen of the holding position 3 is the process-requiring specimen since the information of the measurement order exists in the specimen processing table PT and the measurement status is "not measured". Therefore, the specimen conveyance destination determining process S106 is executed by the CPU 51a.

In the specimen conveyance destination determining process, the process-requiring specimen in which the number of the holding position is the smallest in the specimen processing table PT is selected by the CPU 51a (step S201). The specimen of the holding position 3 is then selected, and whether or not the first measurement unit 2 is in the specimen retrievable state is determined by the measurement unit state data region S1 of the RAM 51c (step S202). The information of "specimen unretrievable/unreturnable" is held in the measurement unit state data region S1. Therefore, the first measurement unit 2 is determined as specimen unretrievable (NO in step S202), and whether or not the second measurement unit 2 is in the specimen retrievable state is determined by the measurement unit state data region S2 of the RAM 51c (step S204). The information "specimen unretrievable/unreturnable" is held in the measurement unit state data region S2. Therefore, the CPU 51a determines that the second measurement unit 3 is specimen unretrievable (NO in step S204), the conveyance destination is determined as "none" (step S206), and the process is returned to the callout address of the specimen conveyance destination determining process.

The CPU 51a determines whether or not the determined conveyance destination is the first measurement unit 2 or the second measurement unit 3 (step S107), and determines whether or not a measurement unit in which the device state is "specimen returnable" exists (step S112) since the determined conveyance destination is "none" (NO in step S107). Since "specimen unretrievable/unreturnable" is stored in both measurement unit state data regions S1, S2 (NO in step S112), the CPU 51a references the specimen processing table PT and determines whether or not the holding position at where the measurement unit is unconfirmed exists (step S115). As the measurement order of the holding positions 4 to 10 is unconfirmed (YES in step S115), the holding position 4 of the smallest number of the holding positions in which the measurement order is unconfirmed is positioned at the reading position 43d (step S116), and the specimen container T is held at the holding position (YES in step S117), the specimen container T is detected by the specimen container sensor 45. Therefore, the specimen ID is read by the barcode reading unit 44 from the barcode of the specimen of the holding position 4 (step S118), and the measurement order acquiring process is executed.

In the measurement order acquiring process, the measurement order of the specimen of the holding position 4, that is, the measurement order including the CBC+DIFF item is acquired from the host computer 6 by the CPU 51a (steps S301, S302). The specimen processing table PT is then updated (step S303), "1" is stored in the field F2 of the presence of the specimen container T in the row of the holding position 4 of the specimen processing table PT, the information indicating "CBC+DIFF" is stored in the field F3 of the measurement order, and the information indicating "not measured" is stored in the field F4 of the measurement status.

Figure 18G:
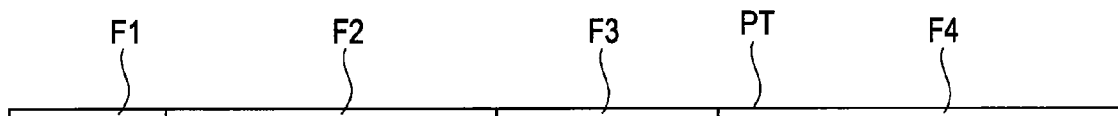
FIG. 18G is a view schematically showing one example of a state of the specimen processing table.

As shown in FIG. 17, the specimen conveyance control process is continuously executed in parallel with the measurement order acquiring process. That is, the processes after step S103 are repeatedly executed, and the measurement orders of the specimens of the remaining holding positions 5 to 10 are acquired (steps S103 to S118, S301 to S303). The state of the updated specimen processing table PT is shown in FIG. 18G.

That is, when the specimen barcode reading is not performed on the specimen container T of the holding positions 3 to 10, and the first measurement unit 2 and the second measurement unit 3 are both executing the specimen measurement, the first measurement unit 2 and the second measurement unit 3 cannot be selected as the specimen supply destination, the specimen containers T of the holding positions 3 to 10 are sequentially conveyed to the reading position 43d, and the specimen barcode reading is sequentially executed on the specimen containers T of the holding positions 3 to 10.

This will be described using FIG. 9. The sample rack L is conveyed until the holding position 3 is positioned at the reading position 43d, and the specimen ID is read by the barcode reading unit 44 from the barcode of the specimen container T of the holding position 3 of the sample rack L (step S001). At this time point, the first measurement unit 2 is performing the processing of the specimen (YES in step S002) and the second measurement unit 3 is also performing the processing of the specimen (YES in step S003), and thus the sample rack L is conveyed until the specimen container T of the holding position 4 is positioned at the reading position 43d (step S008). Since the specimen ID is read by the barcode reading unit 44 from the barcode of the specimen container T of the holding position 4 (step S001), and both the first measurement unit 2 and the second measurement unit 3 are executing the processing of the specimen (YES in step S002 and step S003), the specimen container T of the holding position 5 is conveyed to the reading position 43d (step S008), and the specimen barcode is read (step S001). Similarly, the specimen containers T of the holding positions 6 to 10 are also sequentially conveyed to the reading position 43d (step S008), and the specimen barcode is read (step S001).

If the specimen retrieval process related to the specimen container T of the holding position 1 (or 2) terminates during the reading of the specimen barcode and acquisition of the measurement order for the specimens of the holding positions 3 to 10, the information "specimen returnable" is input to the state queue Q1 (or Q2) (step S406 of FIG. 14). Therefore, the information "specimen returnable" is immediately stored in the measurement unit state data region S1 (or S2) by the CPU 51a, and the sample rack L is conveyed to the first measurement unit 2 (or second measurement unit 3) (step S113 of FIG. 10A) to be executed with the specimen return process by the first measurement unit 2 (or second measurement unit 3) (step S114). The specimen container T is thereby returned to the holding position 1 (or 2) of the sample rack L. After the specimen container T is returned to the sample rack L, the specimen barcode reading is resumed, and the specimen barcode related to the specimens of the remaining holding positions are read.

In the present example, assume that the reading of the barcode and the acquisition of the measurement order of the specimens of the holding positions 3 to 10 are completed before the specimen retrieval process of the holding positions 1, 2 is completed.

When the process of step S405 with respect to the specimen container T of the holding position 1 is completed thereafter, the information "specimen returnable" is input to the state queue Q1 by the CPU 51a (step S406). Furthermore, the CPU 51a stores the information "specimen returnable" input the last to the state queue Q1 in the measurement unit state data region S1 (step S103). As shown in FIG. 18G, the sample rack L is not dischargeable (NO in step S104) since the data of the measurement status corresponding to the holding positions 1, 2 is "during specimen retrieval", and the data of the measurement status of the holding positions 3 to 10 is "not measured". The specimens of the holding positions 3 to 10 are process-requiring specimens since the information of the measurement order exists in the specimen processing table PT and the measurement status is "not measured" (YES in step S105). Therefore, the specimen conveyance destination determining process S106 is executed by the CPU 51a.

In the specimen conveyance destination determining process, the specimen of the holding position 3 is first selected by the CPU 51a in step S201. The information "specimen returnable" is stored in the measurement unit state data region S1 of the RAM 51c, and the information "specimen unretrievable/unreturnable" is stored in the measurement unit state data region S2. Therefore, both the first measurement unit 2 and the second measurement unit 3 are determined as specimen unretrievable (NO in step S202 and S204), "none" is determined for the conveyance destination (step S206), and the process returns to the callout address of the specimen conveyance destination determining process S106.

The CPU 51a determines whether or not the determined conveyance destination is the first measurement unit 2 or the second measurement unit 3 (step S107), where the determined conveyance destination is "none" (NO in step S107), and thus whether or not the measurement unit in which the device state is "specimen returnable" exists is determined (step S112). Since "specimen returnable" is stored in the measurement unit state data region S1 (YES in step S112), the CPU 51a references the specimen processing table PT and conveys the sample rack L to position the holding position 1 corresponding to the record in which "during specimen retrieval (first measurement unit)" is stored in the field F4 at the first specimen supply position 43a (step S113).

The CPU 51a executes the specimen return process by the first measurement unit 2 (step S114). The first measurement unit 2 is thereby controlled, and the retrieved specimen container T is discharged from the first measurement unit 2 and returned to the sample rack L (steps S601 to S603). The CPU 51a inputs the "specimen retrievable" to the state queue Q1 of the RAM 51c (step S604), and changes the data of the measurement status corresponding to the holding position 1 in the specimen processing table PT to "measured" (step S605). Thereafter, the CPU 51a returns the process to the callout address of the specimen return process.

The process of step S103 is again executed by the CPU 51a. At this time point, the data input last to the state queue Q1 is "specimen returnable", and thus the information "specimen retrievable" is stored in the measurement unit state data region S1 in the process of step S103. That is, "specimen retrievable" is stored in the measurement unit state data region S1, and "specimen unretrievable/unreturnable" is stored in the measurement unit state data region S2.

At this time point, the data of the measurement status corresponding to the holding position 2 is "during specimen retrieval", and the data of the measurement status of the holding positions 3 to 10 is "not measured", and thus the sample rack L is not dischargeable (NO in step S104). Furthermore, the specimens of the holding positions 3 to 10 are process-requiring specimens since the information of the measurement order exists in the specimen processing table PT and the measurement status is "not measured" (YES in step S105). Therefore, the specimen conveyance destination determining process S106 is executed by the CPU 51a.

In the specimen conveyance destination determining process, the specimen of the holding position 3 is selected by the CPU 51a in step S201. The information "specimen retrievable" is held in the measurement unit state data region S1. Therefore, the first measurement unit 2 is determined as specimen retrievable (YES in step S202), the first measurement unit 2 is determined as the conveyance destination (step S203), and the process is returned to the callout address of the specimen conveyance destination determining process S106.

Whether or not the determined conveyance destination is the first measurement unit 2 or the second measurement unit 3 is determined by the CPU 51a (step S107), where the specimen of the holding position 3 is conveyed to the first specimen supply position 43a (step S108) since the conveyance destination is determined as the first measurement unit 2 (YES in step S107).

That is, if the specimen barcode reading is performed on the specimen container T of the holding position 3, the first measurement unit 2 is not executing the specimen measurement, and the second measurement unit 3 is executing the specimen measurement, the first measurement unit 2 is selected as the specimen supply destination, and the specimen container T is conveyed to the first specimen supply position 43a to supply the specimen container T of the holding position 3 to the first measurement unit 2.

This will be described with reference to FIG. 9. The specimen ID is already read by the barcode reading unit 44 from the barcode of the specimen container T of the holding position 3 of the sample rack L (step S001). At this time point, the first measurement unit 2 does not perform the processing of the specimen (NO in step S002) and the second measurement unit 3 performs the processing of the specimen (YES in step S004). Therefore, the specimen container T of the holding position 3 is conveyed to the first specimen supply position 43a (step S006).

Returning back to FIG. 10A, "specimen unretrievable/unreturnable" is input to the state queue Q1 of the RAM 51c by the CPU 51a (step S109), and the measurement status of the holding position 3 of the specimen processing table PT is changed to "during specimen retrievable (first measurement unit)" (step S110). The specimen container T of the holding position 3 at the first specimen supply position 43a is taken out from the sample rack L (step S111). Thereafter, the specimen retrieval process by the first measurement unit 2 is executed, and the specimen container T is retrieved inside the first measurement unit 2 (steps S401 to 405). As shown in FIG. 17, the specimen retrieval process of the specimen container T of the holding position 2 is also executed in parallel.

When the process of step S405 with respect to the specimen container T of the holding position 2 is completed thereafter, the information "specimen returnable" is input to the state queue Q2 by the CPU 51a (step S406), and the specimen measurement process is executed. Furthermore, the CPU 51a stores the information "specimen returnable" input the last to the state queue Q2 in the measurement unit state data region S1 (step S103). The sample rack L is not dischargeable (NO in step S104) since the data of the measurement status corresponding to the holding positions 2, 3 is "during specimen retrieval", and the data of the measurement status of the holding positions 4 to 10 is "not measured". The specimens of the holding positions 4 to 10 are process-requiring specimens since the information of the measurement order exists in the specimen processing table PT and the measurement status is "not measured" (YES in step S105). Therefore, the specimen conveyance destination determining process S106 is executed by the CPU 51a.

In the specimen conveyance destination determining process, the specimen of the holding position 4 is first selected by the CPU 51a in step S201. The information "specimen unretrievable/unreturnable" is stored in the measurement unit state data region S1 of the RAM 51c, and the information "specimen returnable" is stored in the measurement unit state data region S2. Therefore, both the first measurement unit 2 and the second measurement unit 3 are determined as specimen unretrievable (NO in step S202 and S204), "none" is determined for the conveyance destination (step S206), and the process returns to the callout address of the specimen conveyance destination determining process S106.

The CPU 51a determines whether or not the determined conveyance destination is the first measurement unit 2 or the second measurement unit 3 (step S107), where the determined conveyance destination is "none" (NO in step S107), and thus whether or not the measurement unit in which the device state is "specimen returnable" exists is determined (step S112). Since "specimen returnable" is stored in the measurement unit state data region S2 (YES in step S112), the CPU 51a references the specimen processing table PT and conveys the sample rack L to position the holding position 2 corresponding to the record in which "during specimen retrieval (second measurement unit)" is stored in the field F4 at the second specimen supply position 43b (step S113).

The CPU 51a then executes the specimen return process by the second measurement unit 3 (step S114). The second measurement unit 3 is thereby controlled, and the retrieved specimen container T is discharged from the second measurement unit 3 and returned to the sample rack L (steps S601 to S603). The CPU 51a inputs the "specimen retrievable" to the state queue Q2 of the RAM 51c (step S604), and changes the data of the measurement status corresponding to the holding position 2 in the specimen processing table PT to "measured" (step S605). Thereafter, the CPU 51a returns the process to the callout address of the specimen return process.

Similar to the holding positions 1 to 3, the retrieval of the specimen container T of the holding position 4 by the second measurement unit 3, the measurement of the specimen of the holding position 3 by the first measurement unit 2, the return of the specimen container T of the holding position 3 from the first measurement unit 2, the retrieval of the specimen container T of the holding position 5 by the first measurement unit 2, the measurement of the specimen of the holding position 4 by the second measurement unit 3, the return of the specimen container T of the holding position 4 from the second measurement unit 3, the retrieval of the specimen container T of the holding position 6 by the second measurement unit 3, the measurement of the specimen of the holding position 5 by the first measurement unit 2, the return of the specimen container T of the holding position 5 from the first measurement unit 2, the retrieval of the specimen container T of the holding position 7 by the first measurement unit 2, the measurement of the specimen of the holding position 6 by the second measurement unit 3, the return of the specimen container T of the holding position 6 from the second measurement unit 3, the retrieval of the specimen container T of the holding position 8 by the second measurement unit 3, the measurement of the specimen of the holding position 7 by the first measurement unit 2, the return of the specimen container T of the holding position 7 from the first measurement unit 2, the retrieval of the specimen container T of the holding position 9 by the first measurement unit 2, the measurement of the specimen of the holding position 8 by the second measurement unit 3, the return of the specimen container T of the holding position 8 from the second measurement unit 3, the retrieval of the specimen container T of the holding position 10 by the second measurement unit 3, the measurement of the specimen of the holding position 9 by the first measurement unit 2, the return of the specimen container T of the holding position 9 from the first measurement unit 2, the measurement of the specimen of the holding position 10 by the second measurement unit 3, and the return of the specimen container T of the holding position 10 from the second measurement unit 3 are executed in such an order while partially overlapping each other.

That is, the reading of specimen barcode is executed in such an order on the specimen container of the holding positions 3 to 10, and the specimen containers T of the holding positions 3 to 10 are sequentially supplied to the first measurement unit 2 or the second measurement unit 3 in the order of specimen barcode reading.

According to such a configuration, the sample rack L is conveyed by the specimen conveyance unit 4 to position one holding position of the sample rack L at the barcode reading position 43d, detection of the presence of the specimen container T at the holding position and the reading of the specimen barcode are performed, and thereafter, the sample rack L is conveyed to the first specimen supply position 43a or the second specimen supply position 43b to allocate the specimen container T performed with the reading of the specimen barcode to the first measurement unit 2 and the second measurement unit 3. Thus, the device configuration can be simplified since only one barcode reader 44 common to the first measurement unit 2 and the second measurement unit 3 needs to be provided. A plurality of specimen containers T held by the sample rack L is allocated to the first measurement unit 2 and the second measurement unit 3, and the measurements of the specimens by the first measurement unit 2 and the second measurement unit 3 are performed in parallel, and thus the specimen can be efficiently processed (measured).

In the specimen processing device 1 according to the present embodiment, the specimen containers T held by the sample rack L and completed with the detection of the presence of the specimen container T and the reading of the specimen barcode are conveyed to the first specimen supply position 43a or the second specimen supply position 43b before the detection of the presence of the specimen container T and the reading of the specimen barcode are completed with respect to all specimen containers T held by the sample rack L, and thus the measurement of the specimen can be started at an early stage and the processing efficiency of the specimen enhances.

In the specimen processing device 1 according to the present embodiment, the barcode reading position 43d is arranged between the first specimen supply position 43a and the second specimen supply position 43b, where the specimen container sensor 45 detects the presence of the specimen container T positioned at the barcode reading position 43d, and the barcode reading unit 44 performs the reading of the specimen barcode of the specimen container T positioned at the barcode reading position 43d. Thus, the total of the distance from the barcode reading position 43d to the first specimen supply position 43a, and the distance from the barcode reading position 43d to the second specimen supply position 43b becomes small compared to when the barcode reading position 43d is outside the region between the first specimen supply position 43a and the second specimen supply position 43b. Therefore, compared to the above case, the conveyance distance of when a plurality of specimen containers T held by the sample rack L is distributed to the first measurement unit 2 and the second measurement unit 3 can be reduced, and furthermore, the lifespan of the specimen conveyance unit 4 can be extended.

In the specimen processing device 1 according to the present embodiment, the sample rack L is conveyed, and the detection of the presence of the specimen container T to be subjected to the reading of specimen barcode and the reading of the specimen barcode by the barcode reader 44 are executed while the specimen is being retrieved in the first measurement unit 2 (or the second measurement unit 3). Therefore, the retrieval of the specimen container T and the detection of the presence of the specimen container T as well as the reading of the specimen barcode can be performed in parallel, and hence the operation efficiency of the entire device is high. As shown in FIG. 16, after the first measurement unit 2 starts to retrieve the specimen of the holding position 1 and until the second measurement unit 3 ends the measurement of the specimen of the holding position 10, both the first measurement unit 2 and the second measurement unit 3 barely have time in which the retrieval of the specimen, the return of the specimen container T, the detection of the specimen container T, the reading of the specimen barcode, or the measurement of the specimen is not being performed, and thus the specimen can be efficiently measured.

Furthermore, the specimen processing device 1 has a configuration of performing the detection of the specimen container T and the reading of the specimen barcode with respect to a plurality of holding positions of the sample rack L while the retrieval of one specimen by the first measurement unit 2 (or second measurement unit 3) is being carried out. Thus, the processing of the specimen can be efficiently performed compared to the configuration of performing the reading the identification information (specimen ID) only with respect to a certain specimen container at a predetermined position from the position of the specimen while retrieving such one specimen as in the prior art.

In the specimen analyzer 1, whether or not the first measurement unit 2 or the second measurement unit 3 is in a specimen retrievable state is determined by the information processing unit 5, and then the sample rack L is conveyed to the measurement unit in the specimen retrievable state to have the relevant measurement unit retrieve the specimen container T. Thus, the time until the measurement unit is in the specimen retrievable state does not need to be waited after conveying the sample rack L to the relevant measurement unit, and hence the specimen can be more efficiently processed.

Furthermore, in the specimen analyzer 1, the specimen container is shaken in the first measurement unit 2 or the second measurement unit 3 to stir the specimen while retrieving the specimen container T into the first measurement unit 2 or the second measurement unit 3. Since such stirring of specimen requires a time of about a few dozen seconds, in the specimen processing device 1, the sample rack L is conveyed and the process is executed on other specimen containers T held at the relevant sample rack L while the specimen retrieval process including the stirring process of the specimen is being executed by the first measurement unit 2 or the second measurement unit 3 to efficiently process the specimen.

In the specimen analyzer 1, if the reading of the specimen barcode is executed once on the specimen container T, the relevant specimen container T can be conveyed without performing the reading of the specimen barcode of the relevant specimen container T and the reading of the rack barcode of the sample rack L. Therefore, the conveyance operation of the specimen container T can be efficiently carried out.

In the specimen analyzer 1, the specimen barcode reading of all specimen containers T does not need to be performed all at once, and thus a barcode reading unit of a complex configuration capable of simultaneously reading the specimen barcodes of a plurality of specimen containers T is not necessary.

In the specimen processing device 1, the specimen container T held at the sample rack L and completed with the detection of the presence of the specimen container T and the reading of the specimen barcode can be conveyed to the first specimen supply position 43a or the second specimen supply position 43b before the detection of the presence of the specimen container T and the reading of the specimen barcode are completed with respect to all specimen containers T held at the sample rack L, and thus the measurement of the specimen can be started at an early stage and the processing efficiency of the specimen can be enhanced.

Furthermore, in the specimen processing device 1, the sample rack L can be conveyed and the detection of the presence of the specimen container T, which is the target of specimen barcode reading, and the reading of the specimen barcode by the barcode reader 44 can be executed while the specimen is being retrieved in the first measurement unit 2 (or the second measurement unit 3) by determining the conveyance path. Therefore, the retrieval of the specimen container T, and the detection of the presence of the specimen container T as well as the reading of the specimen barcode can be performed in parallel, and hence the operation efficiency of the entire device is high. As shown in FIG. 17, after the first measurement unit 2 starts to retrieve the specimen of the holding position 1 and until the second measurement unit 3 ends the measurement of the specimen of the holding position 10, both the first measurement unit 2 and the second measurement unit 3 barely have time in which the retrieval of the specimen, the return of the specimen container T, the detection of the specimen container T, the reading of the specimen barcode, or the measurement of the specimen is not being performed, and thus the specimen can be efficiently measured.

Other Embodiments

In the embodiment described above, the barcode reading position 43d is arranged between the first specimen supply position 43a and the second specimen supply position 43b, and the barcode reading unit 44 reads the specimen barcode of the specimen container T positioned at the barcode reading position 43d, but this is not the sole case. The barcode reading position maybe arranged outside arrange between the first specimen supply position and the second specimen supply position, the reading of the specimen barcode of the specimen container positioned at the barcode reading position may be performed and then the specimen container T completed with the reading of the specimen barcode may be conveyed to the first specimen supply position or the second specimen supply position.

In the embodiment described above, the first measurement unit 2 and the second measurement unit 3 respectively retrieves the specimen container T inside the unit, and aspirates the specimen from the specimen container T inside the unit, but this is not the sole case. The first measurement unit may be configured to aspirate the specimen directly from the specimen container T at the first specimen supply position, and the second measurement unit may be configured to aspirate the specimen directly from the specimen container T at the second specimen supply position.

Furthermore, in the above-described embodiment, the specimen processing device 1 is configured to include two measurement units, the first measurement unit 2 and the second measurement unit 3, but is not limited thereto. The specimen processing device may include three or more measurement units, and the reading of the specimen barcode may be performed on the specimen container T held at the sample rack L and the sample rack L may be conveyed to thereafter supply the specimen container T completed with the reading of the specimen barcode to one of the three or more measurement units.

In the above-described embodiment, a configuration of performing the detection of the presence of the specimen container T and the reading of the specimen barcode with respect to some of the plurality of specimen containers T held at the sample rack L, and thereafter conveying the specimen container T completed with the detection of the presence of the specimen container T and the reading of the specimen barcode to the first specimen supply position 43*a* or the second specimen supply position 43*b* has been described, but is not limited thereto. The barcode reading unit 44 may not be arranged, and the specimen container T may be conveyed to the first specimen supply position 43*a* or the second specimen supply position 43*b* after performing only the detection of the presence of the relevant specimen container T, or the specimen container sensor 45 may not be arranged, and the specimen container T may be conveyed to the first specimen supply position 43*a* or the second specimen supply position 43*b* after performing only the reading of the specimen barcode. In place of the detection of the presence of the specimen container T and the reading of the specimen barcode, whether a predetermined amount of specimen is accommodated in the specimen container T may be detected and such a specimen container T may be conveyed to the first specimen supply position 43*a* or the second specimen supply position 43*b*.

Furthermore, whether a predetermined amount of specimen is accommodated in the specimen container T may be detected with either one of or both of the detection of the presence of the specimen container T and the reading of the specimen barcode, and such a specimen container T may be conveyed to the first specimen supply position 43*a* or the second specimen supply position 43*b*.

The detection of the presence of the specimen container T and the reading of the specimen barcode may be performed on all of the plurality of specimen containers T held at the sample rack L, and then such specimen containers T may be conveyed to the first specimen supply position 43*a* or the second specimen supply position 43*b*.

In the above-described embodiment, the specimen processing device 1 is configured to include two measurement units, the first measurement unit 2 and the second measurement unit 3, but is not limited thereto. The specimen processing device may include three or more measurement units, and the detection of the presence of the specimen container T and the reading of the specimen barcode may be performed on the specimen container T held at the sample rack L and the sample rack L may be conveyed to thereafter supply the specimen container T completed with the detection of the presence of the specimen container T and the reading of the specimen barcode to one of the three or more measurement units.

In the above-described embodiment, the specimen processing device 1 is a multi-item blood cell analyzer, but is not limited thereto. In the specimen processing device other than the multi-item blood cell analyzer such as the blood coagulation measurement device, immune analyzer, urinary formed element analyzer, urine qualitative analyzer, or a blood smear producing device, the processing of the specimen accommodated in the specimen container may be performed after performing a predetermined detection process on the specimen container held at the sample rack.

In the embodiment described above, a configuration of executing all processes of the computer program 54*a* with a single computer 5*a* has been described, but this is not the sole case, and a distributed system of distributing the processes similar to the computer program 54*a* to a plurality of devices (computers) and executing the same may be adopted.

In the above-described embodiment, a configuration in which the specimen conveyance unit 4 conveys the specimen to two measurement units 2, 3 arranged in a single specimen processing device 1 has been described, but is not limited thereto, and two independent measurement devices each including the specimen conveyance unit maybe arranged, the specimen conveyance units may be connected to form one conveyance line, the sample rack may be conveyed to each measurement device by the conveyance line, and the sample rack L may be conveyed and the process may be performed on another specimen container while the specimen container is being retrieved to at least one measurement device.

What is claimed is:

1. A specimen processing device comprising:
   a first processing unit for processing a specimen;
   a second processing unit for processing a specimen;
   a conveyance unit for conveying a specimen rack in a first direction from a first position where the specimen is retrieved by the first processing unit to a second position where the specimen is retrieved by the second processing unit, and a second direction from the second position to the first position, the specimen rack holding a plurality of sample containers;
   a detector common to the first and second processing units for executing a predetermined detection process with respect to the sample containers held by the specimen rack; and
   a conveyance controller for controlling the conveyance unit to convey some sample containers of the detected sample containers executed with the detection process by the detector to the first position, and to convey the other sample containers of the detected sample containers to the second position, the some sample containers and the other sample containers being held by a common specimen rack.

2. The specimen processing device according to claim 1, wherein the conveyance controller controls the conveyance unit to convey at least one of the detected sample containers to the first position or the second position before the detection process on all sample containers held by the specimen rack is completed.

3. The specimen processing device according to claim 1, wherein the conveyance controller controls the conveyance unit to convey a first detected sample container to the first processing unit and a second detected sample container to the second processing unit after the detection process on the first and second detected sample containers held by the specimen rack is completed and before the detection process on a third sample container held following the first and second detected sample containers by the specimen rack is executed.

4. The specimen processing device according to claim 1, wherein the detector is arranged between the first position and the second position.

5. The specimen processing device according to claim 1, wherein
   the first processing unit includes a first specimen container retrieving portion for retrieving the detected sample container conveyed to the first position from the specimen rack, and a first aspirating portion for aspirating the specimen from the detected sample container retrieved by the first specimen container retrieving portion; and the conveyance controller controls the conveyance unit to convey a non-detected sample container not executed with the detection process to the detector after the detected sample container is retrieved from the specimen rack by the first specimen container retrieving portion.

6. The specimen processing device according to claim 1, wherein the conveyance controller acquires first processing status information indicating a processing status of a specimen by the first processing unit and second processing status information indicating a processing status of a specimen by the second processing unit, and controls the conveyance unit to convey the detected sample container to the first position or the second position based on the first processing status information and the second processing status information.

7. The specimen processing device according to claim 1, wherein the detector detects specimen identification information from a sample container as the detection process.

8. The specimen processing device according to claim 1, wherein the detector detects presence of a sample container as the detection process.

9. The specimen processing device according to claim 1, wherein the first processing unit is configured to perform measurement of a clinical specimen.

10. A specimen analyzer comprising:
a first processing unit for:
performing a specimen process comprising a retrieval of a sample container at a first position from a specimen rack, a stirring of a specimen, an aspiration of the specimen from the sample container and a return of the sample container to the specimen rack, and a specimen measurement, or
performing a specimen process comprising an aspiration of a specimen from a sample container at a first position held by a specimen rack and a specimen measurement;
a second processing unit for:
performing a specimen process comprising a retrieval of a sample container at a second position from a specimen rack, a stirring of a specimen, an aspiration of the specimen from the sample container and a return of the sample container to the specimen rack, and a specimen measurement, or
performing a specimen process comprising an aspiration of a specimen from a sample container at a second position held by a specimen rack and a specimen measurement;
a conveyance unit for conveying a specimen rack in a first direction from the first position to the second position and a second direction from the second position to the first position, the specimen rack holding a plurality of sample containers;
a detector common to the first and second processing units for executing a predetermined detection process with respect to the sample containers held by the specimen rack; and a conveyance controller for controlling the conveyance unit to convey one sample container executed with the detection process by the detector to the first position when the first processing unit and the second processing unit are not performing the specimen process, and to convey another sample container executed with the detection process by the detector to the second position when the first processing unit is performing the specimen process and the second processing unit is not performing the specimen process, the one sample container and another sample container being held by a common specimen rack.

11. The specimen analyzer according to claim 10, wherein the conveyance controller controls the conveyance unit to convey at least one of the detected sample containers to the first position or the second position before the detection process on all sample containers held by the specimen rack is completed.

12. The specimen analyzer according to claim 10, wherein the conveyance controller controls the conveyance unit to convey a first detected sample container to the first processing unit and a second detected sample container to the second processing unit after the detection process on the first and second detected sample containers held by the specimen rack is completed and before the detection process on a third sample container held following the first and second detected sample containers by the specimen rack is executed.

13. The specimen analyzer according to claim 10, wherein the detector is arranged between the first position and the second position.

14. The specimen analyzer according to claim 10, wherein the first processing unit includes a first specimen container retrieving portion for retrieving the detected sample container conveyed to the first position from the specimen rack, and a first aspirating portion for aspirating the specimen from the detected sample container retrieved by the first specimen container retrieving portion; and the conveyance controller controls the conveyance unit to convey a non-detected sample container not executed with the detection process to the detector after the detected sample container is retrieved from the specimen rack by the first specimen container retrieving portion.

15. The specimen analyzer according to claim 10, wherein the conveyance controller acquires first processing status information indicating a processing status of a specimen by the first processing unit and second processing status information indicating a processing status of a specimen by the second processing unit, and controls the conveyance unit to convey the detected sample container to the first position or the second position based on the first processing status information and the second processing status information.

16. The specimen analyzer according to claim 10, wherein the detector detects specimen identification information from a sample container as the detection process.

17. The specimen analyzer according to claim 10, wherein the detector detects presence of a sample container as the detection process.

18. The specimen analyzer according to claim 10, wherein the first processing unit is configured to perform measurement of a clinical specimen.

* * * * *